(12) United States Patent
Paschon et al.

(10) Patent No.: US 8,772,453 B2
(45) Date of Patent: Jul. 8, 2014

(54) COMPOSITIONS FOR LINKING ZINC FINGER MODULES

(75) Inventors: David Paschon, Oakland, CA (US); Edward J. Rebar, El Cerrito, CA (US)

(73) Assignee: Sangamo BioSciences, Inc., Richmond, CA (US)

( * ) Notice: Subject to any disclaimer, the term of this patent is extended or adjusted under 35 U.S.C. 154(b) by 326 days.

(21) Appl. No.: 13/068,102

(22) Filed: May 2, 2011

(65) Prior Publication Data

US 2011/0287512 A1 Nov. 24, 2011

Related U.S. Application Data

(60) Provisional application No. 61/343,729, filed on May 3, 2010.

(51) Int. Cl.
*C12N 9/16* (2006.01)
*C12N 1/19* (2006.01)

(52) U.S. Cl.
USPC .......................... 530/350; 435/375; 536/23.4

(58) Field of Classification Search
CPC ........................ C07K 14/4702; C12N 15/1037
USPC .......................... 530/350; 435/375; 536/23.4
See application file for complete search history.

(56) References Cited

U.S. PATENT DOCUMENTS

| | | |
|---|---|---|
| 5,356,802 A | 10/1994 | Chandrasegaran |
| 5,436,150 A | 7/1995 | Chandrasegaran |
| 5,487,994 A | 1/1996 | Chandrasegaran |
| 5,789,538 A | 8/1998 | Rebar et al. |
| 5,925,523 A | 7/1999 | Dove et al. |
| 6,007,988 A | 12/1999 | Choo et al. |
| 6,013,453 A | 1/2000 | Choo et al. |
| 6,140,081 A | 10/2000 | Barbas |
| 6,140,466 A | 10/2000 | Barbas et al. |
| 6,200,759 B1 | 3/2001 | Dove et al. |
| 6,242,568 B1 | 6/2001 | Barbas et al. |
| 6,410,248 B1 | 6/2002 | Greisman et al. |
| 6,453,242 B1 | 9/2002 | Eisenberg et al. |
| 6,479,626 B1 * | 11/2002 | Kim et al. ............. 530/300 |
| 6,534,261 B1 | 3/2003 | Cox et al. |
| 6,599,692 B1 | 7/2003 | Case et al. |
| 6,689,558 B2 | 2/2004 | Case |
| 6,903,185 B2 | 6/2005 | Kim et al. |
| 7,067,317 B2 | 6/2006 | Rebar et al. |
| 7,153,949 B2 | 12/2006 | Kim et al. |
| 7,253,273 B2 | 8/2007 | Collingwood |
| 7,262,054 B2 | 8/2007 | Jamieson et al. |
| 2003/0119023 A1 | 6/2003 | Choo et al. |
| 2004/0197892 A1 | 10/2004 | Moore et al. |
| 2005/0064474 A1 | 3/2005 | Urnov et al. |
| 2006/0063231 A1 | 3/2006 | Li et al. |
| 2006/0188987 A1 | 8/2006 | Guschan et al. |
| 2007/0059795 A1 | 3/2007 | Moore et al. |
| 2007/0134796 A1 | 6/2007 | Holmes et al. |
| 2007/0149770 A1 | 6/2007 | Kim et al. |
| 2007/0218528 A1 | 9/2007 | Miller et al. |
| 2008/0015164 A1 | 1/2008 | Collingwood |
| 2008/0070306 A1 | 3/2008 | Choo et al. |
| 2008/0131962 A1 | 6/2008 | Miller |
| 2008/0159996 A1 | 7/2008 | Ando et al. |
| 2008/0188000 A1 | 8/2008 | Reik et al. |
| 2008/0299580 A1 | 12/2008 | DeKelver et al. |
| 2009/0007300 A1 | 1/2009 | Barbas et al. |
| 2009/0068164 A1 | 3/2009 | Segal et al. |

FOREIGN PATENT DOCUMENTS

| | | |
|---|---|---|
| GB | 2338237 A | 12/1999 |
| WO | WO 95/19431 A1 | 7/1995 |
| WO | WO 96/06166 A1 | 2/1996 |
| WO | WO 98/37186 A1 | 8/1998 |
| WO | WO 98/53057 A1 | 11/1998 |
| WO | WO 98/53058 A1 | 11/1998 |
| WO | WO 98/53059 A1 | 11/1998 |
| WO | WO 98/53060 A1 | 11/1998 |
| WO | WO 98/54311 A1 | 12/1998 |
| WO | WO 00/27878 A1 | 5/2000 |
| WO | WO 01/53480 A1 | 7/2001 |
| WO | WO 01/60970 A2 | 8/2001 |
| WO | WO 01/88197 A2 | 11/2001 |
| WO | WO 02/16536 A1 | 2/2002 |
| WO | WO 02/077227 A2 | 10/2002 |
| WO | WO 02/099084 A2 | 12/2002 |
| WO | WO 03/016496 A2 | 2/2003 |
| WO | WO 03/104414 B2 | 12/2003 |
| WO | WO 2005/061705 A1 | 7/2005 |
| WO | WO 2007/014275 A2 | 1/2007 |
| WO | WO 2007/139898 A2 | 12/2007 |
| WO | WO 2007/139982 A2 | 12/2007 |
| WO | WO 2009/042163 A2 | 4/2009 |
| WO | WO 2011/011767 A1 | 1/2011 |

OTHER PUBLICATIONS

Pomerantz et al. [Science 267: 93-96 (1995)].*
Beerli, et al., "Engineering Polydactyl Zinc-Finger Transcription Factors," *Nature Biotechnology* 20:135-141 (2002).
Bitinate, et al., "FOKI Dimerization Is Required for DNA Cleavage," *PNAS USA* 95:10570-10575 (1998).
Choo, et al., "Advances in Zinc Finger Engineering," *Curr. Opin. Struct. Biol.* 10:411-416 (2000).
Gogos, et al., "Sequence Discrimination by Alternatively Spliced Isoforms of a DNA Binding Zinc Finger Domain," *Science* 257:1951-1955 (1992).
Hockemeyer, et al., "Efficient Targeting of Expressed and Silent Genes in Human ESCS and IPSCS Using Zinc-Finger Nucleases," *Nat Biotechnol* 27:851-857 (2009).

(Continued)

*Primary Examiner* — Tekchand Saidha
(74) *Attorney, Agent, or Firm* — Pasternak Patent Law; Susan Abrahamson; Dahna S. Pasternak

(57) ABSTRACT

Disclosed herein are compositions for linking DNA binding modules to allow for specific and selective binding to module subsites separated by 1 or more base pairs. Also described are methods of making and using compositions comprising these linkers.

15 Claims, 14 Drawing Sheets

(56) References Cited

OTHER PUBLICATIONS

Hoffman, et al., "A New Coactivator Function for Zaci'S C2H2 Zinc Finger DNA-Binding Domain in Selectively Controlling PCAF Activity," *Molecular and Cellular Biology* 28:6078-6093 (2008).

Imanishi, et al., "An Artificial Six-Zinc Finger Peptide With Polyarginine Linker: Selective Binding to the Discontinuous DNA Sequences," *Biochemical and Biophysical Research Communications* 333:167-173 (2005).

Isalan et al., "A Rapid, Generally Applicable Method to Engineer Zinc Fingers Illustrated by Targeting the HIV-1 Promoter," *Nat Biotechnol* 19:656-660 (2001).

Kim, et al., "Chimeric Restriction Endonuclease," *PNAS USA* 91:883-887 (1994).

Kim, et al., "Insertion and Deletion Mutants of FOKI Restriction Endonuclease," *J. Biol. Chem.* 269:31978-31982 (1994).

Kim, et al., "Getting a Handhold on DNA: Design of Poly-Zinc Finger Proteins With Femtomolar Dissociation Constants," *PNAS* 95:2812-2817 (1998).

Li, et al., "Functional Domains in FOK I Restriction Endonuclease," *PNAS USA* 89:4275-4279 (1992).

Li, et al., "Alteration of the Cleavage Distance of FOK I Restriction Endonuclease by Insertion Mutagenesis," *PNAS USA* 90:2764-2768 (1993).

Moore, et al., "Design of Polyzinc Finger Peptides With Structured Linkers," *PNAS* 98:1432-1436 (2001).

Morellet, et al., "Conformational Behaviour of the Active and Inactive Forms of the Nucleocapsid NCP7 of HIV-1 Studied by 1H NMR," *J. Mol Biol* 235:287-301 (1994).

Nagaoka, et al., "Significant Effect of Linker Sequence on DNArecognition by Multi-Zinc Finger Protein," *Biochemical and Biophysical Research Communications* 282:1001-1007 (2001).

Neuteboom, et al., "Effects of Different Zinc Finger Transcription Factors on Genomic Targets," *Biochemical and Biophysical Research Communications* 339:263-270 (2006).

Nomura, et al., "Effects of Length and Position of an Extended Linker on Sequence-Selective DNA Recognition of Zinc Finger Peptides," *Biochemistry* 42:14805-14813 (2003).

Pabo, et al., "Design and Selection of Novel CYS2-HIS2 Zinc Finger Proteins," *Ann. Rev. Biochem.* 70:313-340 (2001).

Robinson, et al., "Optimizing the Stability of Single-Chain Proteins by Linker Length and Composition Mutagenesis," *PNAS* 95:5929-5934 (1998).

Segal, et al., "Custom DNA-Binding Proteins Come of Age: Polydactyl Zinc-Finger Proteins," *Curr. Opin. Biotechnol.* 12:632-637 (2001).

Urnov, et al., "Highly Efficient Endogenous Human Gene Correction Using Designed Zinc-Finger Nucleases," *Nature* 435:646-651 (2005).

Yan, et al., "α-Helical Linker of an Artificial 6-Zinc Finger Peptide Contributes to Selective DNA Binding to a Discontinuous Recognition Sequence," *Biochemistry* 46:8517-8524 (2007).

* cited by examiner

Figure 1A

Host ZFPs Used for Selection

```
                       -1              +6
ZFP 8196   F1   MAERPFQCRICMRNFSRSDNLSVHIRTHTGE
           F2        KPFACDICGRKFAQKINLQVHTKIHTGE
           F3         KPFQCRICMRNFSRSDVLSEHIRTHTGE
           F4         KPFACDICGRKFAQRNHRTTHTKIHLRGS

-1              +6
ZFP 7263   F1   MAERPFQCRICMRNFSRSDNLSVHIRTHTGE
           F2        KPFACDICGRKFARNAHRINHTKIHTGSQ
           F3         KPFQCRICMRNFSRSDDTSEHIRTHTGE
           F4         KPFACDICGRKFAARSTRTNHTKIHLRGS

-1              +6
ZFP 7264   F1   MAERPFQCRICMRNFSRSDTLSEHIRTHTGE
           F2        KPFACDICGRKFAARSTRTTHTKIHTGSQ
           F3         KPFQCRICMRNFSRSDSLSKHIRTHTGE
           F4         KPFACDICGRKFAQRSNLKVHTKIHLRGS
```

← Recognition Helix

Figure 1B

Linker Library Designs Used for Selection

```
                      -1                        +6
ZFP 8196   F1   MAERPFQCRICMRNFSRSDNLSVHIRTHTGE
           F2        KPFACDICGRKFAQKINLQVHTKIHT(NNS)₂₋₁₂
           F3        KPFQCRICMRNFSRSDVLSEHIRTHTGE
           F4        KPFACDICGRKFAQRNHRTTHTKIHLRGS

-1                        +6
ZFP 7263   F1   MAERPFQCRICMRNFSRSDNLSVHIRTHTGE
           F2        KPFACDICGRKFARNAHRINHTKIHT(NNS)₂₋₁₂
           F3        KPFQCRICMRNFSRSDDTSEHIRTHTGE
           F4        KPFACDICGRKFAARSTRTNHTKIHLRGS

-1                        +6
ZFP 7264   F1   MAERPFQCRICMRNFSRSDTLSEHIRTHTGE
           F2        KPFACDICGRKFAARSTRTTHTKIHT(NNS)₂₋₁₂
           F3        KPFQCRICMRNFSRSDSLSKHIRTHTGE
           F4        KPFACDICGRKFAQRSNLKVHTKIHLRGS
```

Randomized Linker → (NNS)₂₋₁₂

Recognition Helix → boxed region from -1 to +6

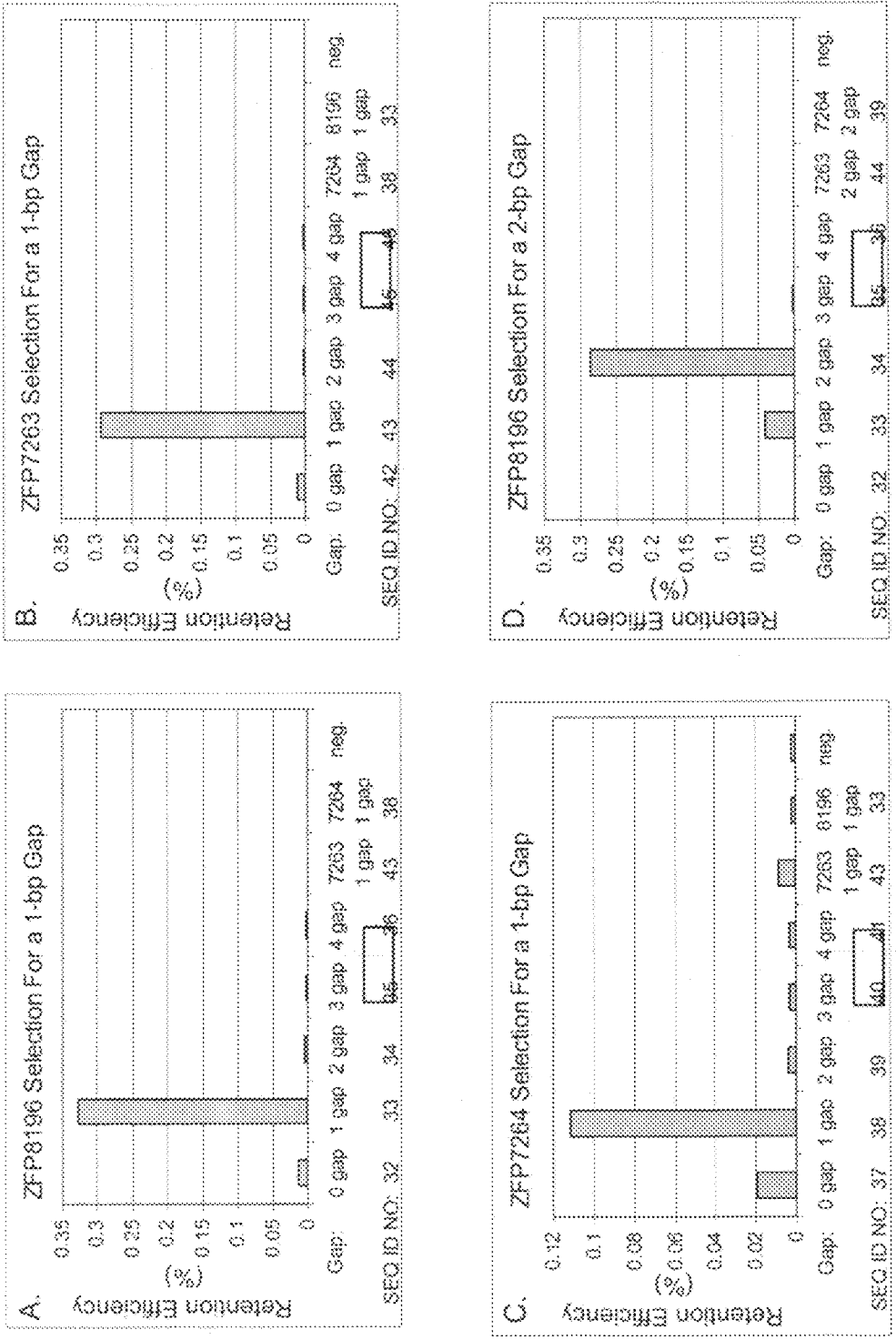

Figure 3

A.
Linkers selected to skip a 1bp gap

ZFP8196

| # clones | | | |
|---|---|---|---|
| 1 | HTKIH | DAPKP | KFFCCRIC |
| 1 | HTKIH | GLHRR | KFFCCRIC |
| 2 | HTKIH | ERAHPP | KFFCCRIC |
| 1 | HTKIH | SHTPRP | KFFCCRIC |
| 1 | HTKIH | QVSTPRP | KFFCCRIC |
| 1 | HTKIH | PRRIAA | KFFCCRIC |
| 1 | HTKIH | PRRAP | KFFCCRIC |
| 1 | HTKIH | NRRAP | KFFCCRIC |
| 1 | HTKIH | SPRLPA | KFFCCRIC |
| 1 | HTKIH | CPRPPTR | KFFCCRIC |
| 1 | HTKIH | SPRSNA | KFFCCRIC |
| 1 | HTKIH | VSPRADCRS | KFFCCRIC |
| 1 | HTKIH | DRRISTQ | KFFCCRIC |

ZFP7263

| # clones | | | |
|---|---|---|---|
| 1 | HTKIH | PRRIP | KFFCCRIC |
| 3 | HTKIH | QPRQIPP | KFFCCRIC |
| 3 | HTKIH | PNRCPPT | KFFCCRIC |
| 2 | HTKIH | YPRPLLA | KFFCCRIC |
| 10 | HTKIH | PLCQRPMKQ | KFFCCRIC |
| 1 | HTKIH | PLCQRRMKQ | KFFCCRIC |

ZFP7264

| # clones | | | |
|---|---|---|---|
| 1 | HTKIH | QLPKP | KFFCCRIC |
| 3 | HTKIH | SRPRP | KFFCCRIC |
| 1 | HTKIH | LPLPRP | KFFCCRIC |
| 4 | HTKIH | VPRPTPP | KFFCCRIC |
| 1 | HTKIH | LPRCFRR | KFFCCRIC |

B.
Linkers selected to skip a 2bp gap

ZFP8196

| # clones | | | |
|---|---|---|---|
| 13 | HTKIH | NACKYRTR | KFFCCRIC |
| 2 | HTKIH | LAPRPYRP | KFFCCRIC |
| 1 | HTKIH | GSPHVRANS | KFFCCRIC |
| 1 | HTKIH | DAAPRPKDT | KFFCCRIC |
| 1 | HTKIH | EYCTRRFRPP | KFFCCRIC |
| 1 | HTKIH | PNPHRYDFS | KFFCCRIC |
| 1 | HTKIH | NTPRPYRLRP | KFFCCRIC |
| 1 | HTKIH | QGKSSRTDR | KFFCCRIC |

Gap Selectivity of Linkers Selected to Skip One Basepair in ZFP8196

Gap Selectivity of Linkers Selected to Skip One Basepair in ZFP7264

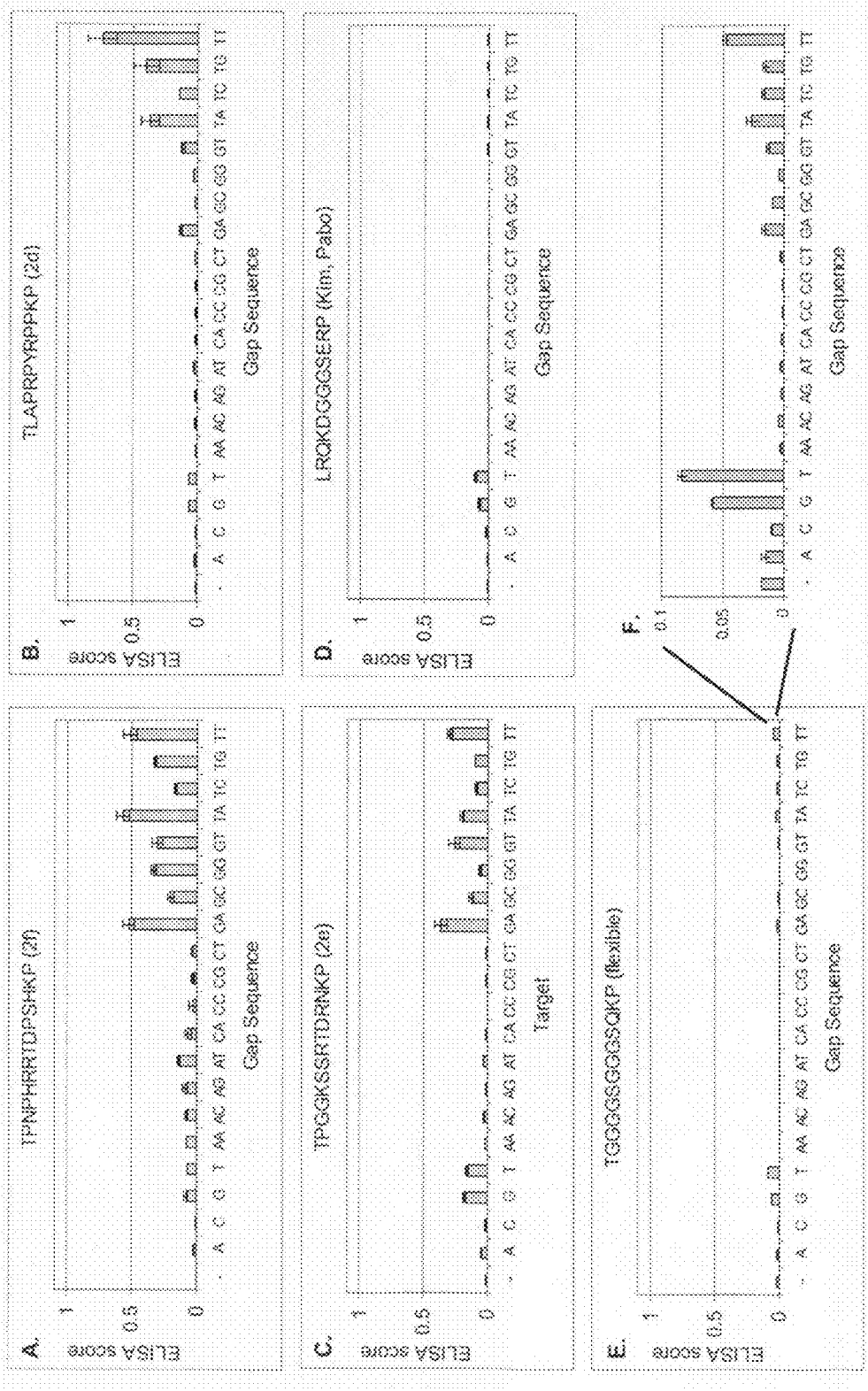

Figure 7

Portability Studies With Linkers Selected to Skip One Basepair

A

| Linker | | ELISA Score | | | | | | | | | | | |
|---|---|---|---|---|---|---|---|---|---|---|---|---|---|
| Sequence | Designation | ZFP1 | ZFP2 | ZFP3 | ZFP4 | ZFP5 | ZFP6 | ZFP7 | ZFP8 | ZFP9 | ZFP10 | ZFP11 | ZFP12 |
| TGGGGSQKP | flexible | 0.75 | 1.08 | 0.21 | 0.26 | 0.08 | 0.05 | 0.05 | 0.05 | 0.05 | 0.05 | 0.05 | 0.05 |
| TVPRPTPPKP | 1e | 1.19 | 1.30 | 1.05 | 1.10 | 0.75 | 0.29 | 0.48 | 0.38 | 0.50 | 0.18 | 0.05 | 0.05 |
| TYPRPIAAKP | 1f | 1.25 | 1.35 | 1.03 | 0.94 | 0.96 | 0.30 | 0.33 | 0.12 | 0.30 | 0.11 | 0.05 | 0.05 |
| TPNRRPAPKP | 1d | 1.20 | 1.08 | 1.04 | 0.83 | 0.85 | 0.25 | 0.39 | 0.28 | 0.24 | 0.12 | 0.05 | 0.05 |
| THPRAPIPKP | 1c | 0.92 | 1.18 | 0.66 | 0.56 | 0.91 | 0.23 | 0.21 | 0.26 | 0.18 | 0.05 | 0.05 | 0.05 |

B

| Linker | | ELISA Score Normalized to Flexible Linker | | | | | | | | | | | | |
|---|---|---|---|---|---|---|---|---|---|---|---|---|---|---|
| Sequence | Designation | ZFP1 | ZFP2 | ZFP3 | ZFP4 | ZFP5 | ZFP6 | ZFP7 | ZFP8 | ZFP9 | ZFP10 | ZFP11 | ZFP12 | Average |
| TGGGGSQKP | flexible | 1.0 | 1.0 | 1.0 | 1.0 | 1.0 | 1.0 | 1.0 | 1.0 | 1.0 | 1.0 | 1.0 | 1.0 | |
| TVPRPTPPKP | 1e | 1.6 | 1.2 | 4.9 | 4.1 | 9.2 | 5.9 | 9.6 | 7.6 | 10.1 | 3.6 | 1.0 | 1.0 | 5.0 |
| TYPRPIAAKP | 1f | 1.7 | 1.2 | 4.9 | 3.5 | 11.7 | 5.9 | 6.5 | 2.3 | 6.0 | 2.2 | 1.0 | 1.0 | 4.0 |
| TPNRRPAPKP | 1d | 1.6 | 1.0 | 4.9 | 3.1 | 10.4 | 4.9 | 7.8 | 5.7 | 4.8 | 2.4 | 1.0 | 1.0 | 4.0 |
| THPRAPIPKP | 1c | 1.2 | 1.1 | 3.1 | 2.1 | 11.2 | 4.7 | 4.3 | 5.3 | 3.6 | 1.0 | 1.0 | 1.0 | 3.3 | underlined values show >4-fold improvement

Figure 8

Portability Studies With Linkers Selected to Skip Two Basepairs

A

| Linker | | ELISA Score | | | | | | |
|---|---|---|---|---|---|---|---|---|
| Sequence | Designation | ZFP13 | ZFP14 | ZFP15 | ZFP16 | ZFP17 | ZFP18 | |
| TGGGGSGGSQKP | flexible | 0.25 | 0.61 | 0.05 | 0.13 | 0.35 | 0.51 | |
| TPNPHRRTDPSHKP | 2f | 0.48 | 1.13 | 0.27 | 0.31 | 0.79 | 0.47 | |
| TLAPRPYRPPKP | 2d | 0.44 | 1.13 | 0.11 | 0.34 | 0.82 | 0.43 | |
| TPGGKSSRTDRNKP | 2e | 0.42 | 0.75 | 0.17 | 0.27 | 0.68 | 0.52 | |

B

| Linker | | ELISA Score Normalized to Flexible Linker | | | | | | |
|---|---|---|---|---|---|---|---|---|
| Sequence | Designation | ZFP13 | ZFP14 | ZFP15 | ZFP16 | ZFP17 | ZFP18 | Average |
| TGGGGSGGSQKP | flexible | 1.0 | 1.0 | 1.0 | 1.0 | 1.0 | 1.0 | |
| TPNPHRRTDPSHKP | 2f | 1.9 | 1.9 | 5.1 | 2.3 | 2.3 | 0.9 | 2.4 |
| TLAPRPYRPPKP | 2d | 1.7 | 1.9 | 2.1 | 2.5 | 2.4 | 0.8 | 1.9 |
| TPGGKSSRTDRNKP | 2e | 1.7 | 1.2 | 3.3 | 2.0 | 2.0 | 1.0 | 1.9 | underlined values show >2-fold improvement

Example Assay Gels

Figure 10

Gene Modification for ZFNs Containing New Linkers Skipping One Basepair

A

| Linker | | Gene Modification (%) | | | | | | | | | | |
|---|---|---|---|---|---|---|---|---|---|---|---|---|
| Sequence | Designation | ZFN1 | ZFN2 | ZFN3 | ZFN4 | ZFN5 | ZFN6 | ZFN7 | ZFN8 | ZFN9 | ZFN10 | ZFN11 | ZFN12 |
| TGGGGSSQKP | flexible | 6.1 | 1.8 | 5.9 | 0.0 | 3.5 | - | 1.1 | - | 0.0 | 0.0 | - | 1.7 |
| TVPRPTPPKP | 1e | 9.5 | 3.8 | 9.3 | 1.0 | 4.9 | - | 2.8 | - | 3.7 | 6.9 | - | 1.9 |
| TVPRPIAAKP | 1f | 9.6 | 4.8 | 12.0 | 1.0 | 2.5 | - | 1.5 | - | 1.5 | 4.2 | - | 2.8 |
| TPNRRPAPKP | 1d | 8.4 | 4.6 | 12.5 | 1.5 | 6.2 | - | 2.6 | - | 4.5 | 7.9 | - | 1.9 |
| THPRAPIPKP | 1c | 9.9 | 3.9 | 12.8 | 1.4 | 5.1 | - | 2.7 | - | NA | 7.4 | - | NA |

B

| Linker | | Gene Modification Normalized to Flexible Linker | | | | | | | | | | | |
|---|---|---|---|---|---|---|---|---|---|---|---|---|---|
| Sequence | Designation | ZFN1 | ZFN2 | ZFN3 | ZFN4 | ZFN5 | ZFN6 | ZFN7 | ZFN8 | ZFN9 | ZFN10 | ZFN11 | ZFN12 | Average |
| TGGGGSSQKP | flexible | 1.0 | 1.0 | 1.0 | - | 1.0 | - | 1.0 | - | - | - | - | 1.0 | |
| TVPRPTPPKP | 1e | 1.6 | 2.1 | 1.6 | >1 | 1.4 | - | 2.4 | - | >3.5 | >7.0 | - | 1.1 | 2.4 |
| TVPRPIAAKP | 1f | 1.6 | 2.7 | 2.0 | >1 | 0.7 | - | 1.4 | - | >1.5 | >4.0 | - | 1.6 | 1.8 |
| TPNRRPAPKP | 1d | 1.0 | 2.6 | 2.1 | >1.5 | 1.8 | - | 2.4 | - | >4.5 | >8.0 | - | 1.1 | 2.8 |
| THPRAPIPKP | 1c | 1.6 | 2.2 | 2.2 | >1.5 | 1.5 | - | 2.5 | - | NA | >7.0 | - | NA | 2.6 |

▓ high expression condition       underlined values show >2-fold improvement

— | no quantifiable signal
NA | not tested

Figure 11

Gene Modification for ZFNs Containing New Linkers Skipping Two Basepairs

A

| Linker | | Gene Modification (%) | | | | | |
|---|---|---|---|---|---|---|---|
| Sequence | Designation | ZFN13 | ZFN14 | ZFN15 | ZFN16 | ZFN17 | ZFN18 |
| TGGGSGGSGQKP | flexible | - | 7.5 | 2.5 | 2.9 | 5.3 | - |
| TPNPHRRTDPSHKP | 2f | - | 17.0 | 5.6 | 7.3 | 4.7 | - |
| TLAPRPYRPPKP | 2d | - | 11.3 | 5.0 | 4.8 | 4.9 | - |
| TPGGKSSRTDRNKP | 2e | - | 11.7 | 5.0 | 4.3 | 6.3 | - |

B

| Linker | | Gene Modification Normalized to Flexible Linker | | | | | | |
|---|---|---|---|---|---|---|---|---|
| Sequence | Designation | ZFN13 | ZFN14 | ZFN15 | ZFN16 | ZFN17 | ZFN18 | Average |
| TGGGSGGSGQKP | flexible | - | 1.0 | 1.0 | 1.0 | 1.0 | - | |
| TPNPHRRTDPSHKP | 2f | - | 2.3 | 2.2 | 2.5 | 0.9 | - | 2.0 |
| TLAPRPYRPPKP | 2d | - | 1.5 | 2.0 | 1.7 | 0.9 | - | 1.5 |
| TPGGKSSRTDRNKP | 2e | - | 1.6 | 2.0 | 1.5 | 1.2 | - | 1.6 |

▓ high expression condition  underlined values show >2-fold improvement

- | no quantifiable signal

Linker Library Design Used For the Secondary Selection For a 2-bp Gap

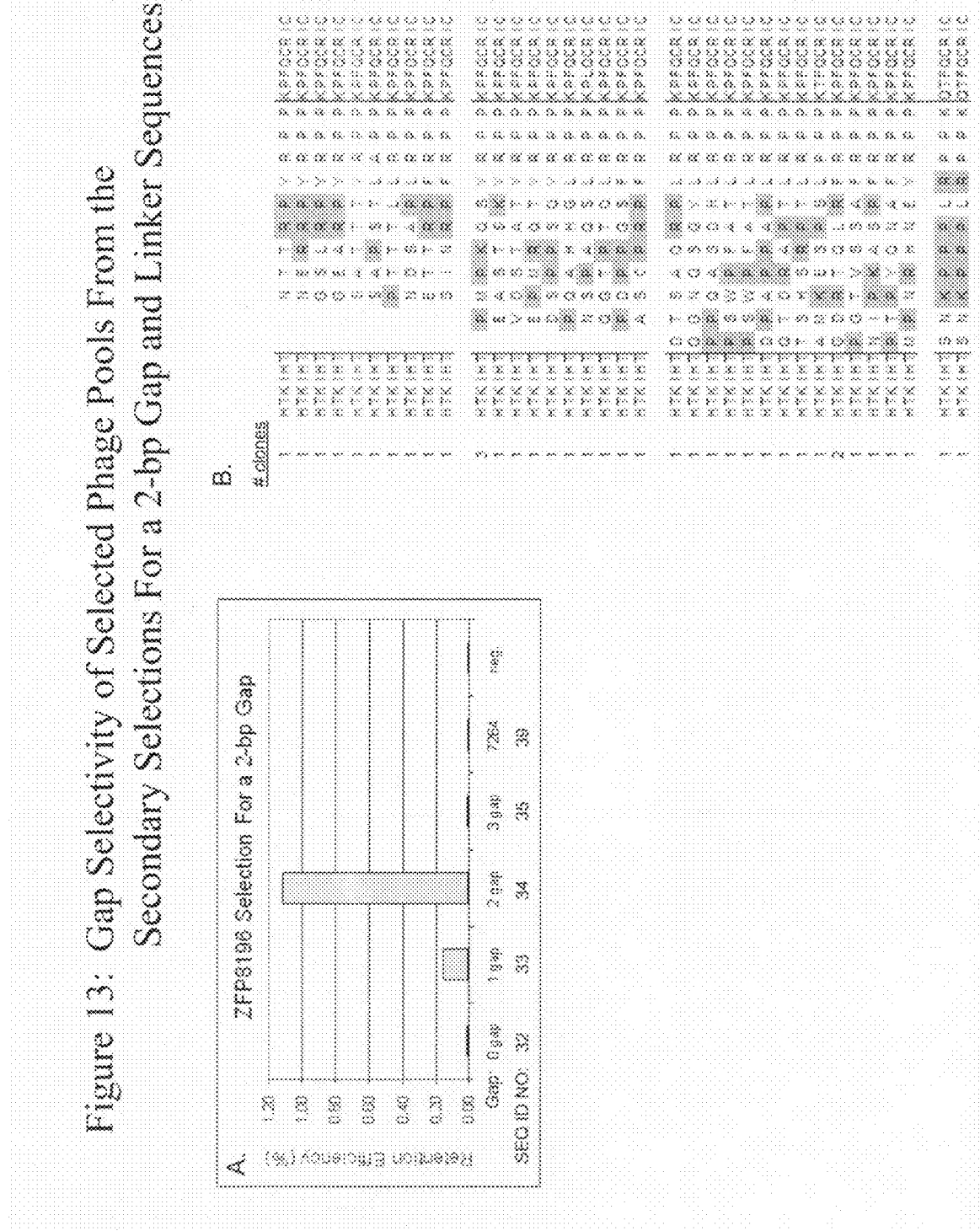
Figure 13: Gap Selectivity of Selected Phage Pools From the Secondary Selections For a 2-bp Gap and Linker Sequences

US 8,772,453 B2

COMPOSITIONS FOR LINKING ZINC FINGER MODULES

CROSS-REFERENCE TO RELATED APPLICATIONS

The present application claims the benefit of U.S. Provisional Application No. 61/343,729, filed May 3, 2010, the disclosure of which is hereby incorporated by reference in its entirety herein.

STATEMENT OF RIGHTS TO INVENTIONS MADE UNDER FEDERALLY SPONSORED RESEARCH

Not applicable.

TECHNICAL FIELD

The present disclosure is in the fields of genome and protein engineering.

BACKGROUND

Zinc-finger proteins with recognition regions that are engineered to bind to selected target sites are regularly linked to other zinc-finger proteins as well as to regulatory domains and used to modify gene expression and genomic target sites. For example, artificial nucleases comprising DNA binding domains operably linked to cleavage domains have been used for targeted alteration of genomic sequences, including, insertion of exogenous sequences, inactivation of one or more endogenous genes, creation of organisms (e.g., animal or crops) and cell lines with altered gene expression patterns, and the like. See, e.g., U.S. Patent Publication Nos. 20050064474; 20060063231; 20070134796; 20080015164 and International Publication No. 2007/139982.

Zinc-finger protein modules (e.g., engineered zinc fingers of one or more fingers) are typically linked to each other using "canonical" linker sequences of 5 amino acids such as TGEKP (SEQ ID NO:1) or longer flexible linkers. See, U.S. Pat. Nos. 6,479,626; 6,903,185; 7,153,949 and U.S. Patent Publication No. 20030119023. However, zinc-finger protein modules linked via these canonical linkers bind most effectively only when there is no gap between the linked module target subsites in the target nucleic acid molecule. Furthermore, previously-described long, flexible linkers designed to allow the linked modules to bind to target sites with 1, 2 or 3 base pair gaps do not distinguish between these different base pair gaps in terms of binding. See, U.S. Pat. Nos. 6,479,626; 6,903,185; 7,153,949 and U.S. Patent Publication No. 20030119023. Thus, there remains a need for methods and compositions for linking zinc-finger modules to each other that improves both the affinity of proteins that span a 1, 2, or 3 bp intermodule gap, as well improve the selectivity of these proteins for binding targets that span a gap of a desired length and do not bind non-selectively to other targets without the gap of that desired length. Linkers for zinc-finger modules that distinguish between 0, 1, 2, 3 or even more base pair gaps between adjacent module subsites would allow for greater design capability of any zinc-finger fusion proteins, including zinc-finger transcription factors (ZFP-TFs) and zinc finger nucleases (ZFNs).

SUMMARY

Disclosed herein are linkers for use in linking DNA-binding modules (e.g., zinc-finger modules) to each other. Also described are fusion proteins, for example zinc-finger proteins comprising these linkers which are in turn fused to regulatory domains such as transcriptional regulatory domains or to nucleases. The disclosure also provides methods of using these fusion proteins and compositions thereof for modulation of gene expression, targeted cleavage of cellular DNA (e.g., endogenous cellular chromatin) in a region of interest and/or homologous recombination at a predetermined region of interest in cells.

Thus, in one aspect, described herein are linkers comprising 5 or more amino acids between the last residue of the amino (N)-terminal finger (typically the carboxy (C)-terminal zinc-coordinating residue) and the first residue of the C-terminal finger (typically the first (N-terminal)-conserved aromatic residue), for example 7-17 amino acids. In certain embodiments, the linker comprises an N-terminal residue, a C-terminal residue, and residues internal to the terminal residues, and further wherein the N-terminal residue or internal residues comprises at least one proline residue, for example a linker comprising the amino acid sequence $X^{N\text{-}term}$—$X_n$—$X^{C\text{-}term}$, wherein X is any amino acid residue, $X_n$ comprises at least 3 amino acid residues and at least one of $X^{N\text{-}term}$ and $X_n$ comprises a proline residue. In certain embodiments, the linker comprises at least two proline residues (e.g., 2, 3, 4 or more). In other embodiments, where the linker comprises at least one proline residue and at least one basic residue (e.g., Arg, His or Lys). In other embodiments, where the linker comprises at least two basic residue (e.g., Arg, His or Lys). In certain embodiments, the linker is one shown in any of Tables 4, 5, 6, 9, 10, 11 or 13.

In another aspect, fusion polypeptides comprising a linker as described herein are provided.

In another aspect, polynucleotides encoding any of the linkers or fusion proteins as described herein are provided.

In yet another aspect, cells comprising any of the polypeptides (e.g., fusion polypeptides) and/or polynucleotides as described herein are also provided.

In a further aspect, organisms (e.g. mammals, fungi and plants) comprising the polypeptides (e.g. fusion polypeptides) and/or polynucleotides as described herein are also provided.

A fusion protein can be expressed in a cell, e.g., by delivering the fusion protein to the cell or by delivering a polynucleotide encoding the fusion protein to a cell. If the polynucleotide is DNA, it is then transcribed and translated to generate the fusion protein. If delivered as an RNA molecule, it is then immediately translated, thus generating the fusion protein. Methods for polynucleotide and polypeptide delivery to cells are presented elsewhere in this disclosure.

These and other aspects will be readily apparent to the skilled artisan in light of disclosure as a whole.

BRIEF DESCRIPTION OF THE DRAWINGS

FIG. 1, panels A and B, show amino sequences of exemplary zinc finger proteins and linkers. FIG. 1A shows the amino acid sequence of each host ZFP (F1-F4 of ZFP8196 shown in SEQ ID NO:130; SEQ ID NO:131; SEQ ID NO:132 and SEQ ID NO:133; F1 to F4 of ZFP7263 shown in SEQ ID NO:134; SEQ ID NO:135; SEQ ID NO:136 and SEQ ID NO:137; F1 to F4 of ZFP7264 shown in SEQ ID NO:138; SEQ ID NO:139; SEQ ID NO:140 and SEQ ID NO:141) used for these studies. Amino acids are designated by single letter code. Each sequence is listed in the amino terminal a carboxy terminal direction, so that the amino terminus of each protein is the first methionine of finger 1, and the carboxy terminus is the final serine of finger 4. "F1", "F2", "F3" and "F4" designate the first, second, third and fourth fingers, respectively, of each protein. Underlining denotes amino acid residues at finger junctions which are conventionally considered to be linker sequence. Recognition helices are boxed. FIG. 1B shows linker library designs in which each library was generated by replacing codons for two or three residues in the central linker with a mixture of two to twelve fully randomized codons. Library codons are denoted by (NNS)2-12. FIG. 1B discloses SEQ ID NOS 130, 47, 132-134, 211, 136-138, 212, and 140-141, respectively, in order of appearance.

FIG. 2, panels A through D, are graphs depicting gap selectivity of phage pools with the indicated zinc finger proteins and linkers. FIG. 2A shows the phage pool selected from the ZFP8196 library using a target with a 1 bp inserted base (ATAAACTGdCAAAAGGC (SEQ ID NO:33) (Table 2A)) that was tested for binding to each ZFP8196 target in Table 2C. FIG. 2B shows the phage pool selected from the ZFP7263 library using a target with a 1 bp inserted base (CCACTCTGh TGGAAGTG (SEQ ID NO:43) (Table 2A)) that was tested for binding to each ZFP7263 target in Table 2C. FIG. 2C shows the phage pool selected from the ZFP7264 library using a target with a 1 bp inserted base (TTAAAGCGh GCTCCGAA (SEQ ID NO:38) (Table 2A)) tested for binding to each ZFP7264 target in Table 2C. FIG. 2D shows the phage pool selected from the ZFP8196 library using a target with a 2 bp inserted base (ATAAACTGdbCAAAAGGC (SEQ ID NO:34) (Table 2A)) tested for binding to each ZFP8196 target in Table 2C. Each test also included two control targets for the other two host ZFPs to rule out nonspecific binding to DNA as well as a negative control sample which did not include a target site. The % of phage which successfully bound each target is indicated. Each phage pool was from the fifth round of selection. Retention efficiency was determined essentially as previously described (Rebar, et al. *Methods in Enzymology*, 1996 (267):129-149).

FIG. 3, panels A and B, show linkers selected for target sites containing the indicated gap. FIG. 3A shows linker sequences selected for skipping a 1 bp gap in the context of ZFP8196, ZFP7263, and ZFP7264 (SEQ ID NOs:142 to 166). FIG. 3B shows linker sequences (SEQ ID NOs:167 to 174) for skipping a 2 bp gap in the context of ZFP8196. Selected linkers are enriched for proline and arginine (shaded). Length preferences are also apparent and depend on the number of skipped bases.

FIGS. 4A-4C depict results from three of the 1 bp gap skipping linkers, (linkers referred to as 1f (SEQ ID NO:54), 1d (SEQ ID NO:56) and 1c (SEQ ID NO:55)). FIG. 4D shows results with a standard flexible linker that has previously been shown to enable modification of an endogenous locus in human cells (TGGGGSQKP, SEQ ID NO:2) (See Hockemeyer et al. (2009) *Nature Biotechnology* 27:851-857) and FIG. 4E depicts the results for a previously published flexible linker (LRQKDERP, SEQ ID NO:3) (See Kim J S & Pabo C O (1998) *Proc Natl Acad Sci USA* 95(6):2812-2817). The selected linkers 1c, 1d and 1f (FIGS. 4A-4C) all show clear preferences for the four target sites with a single base pair gap whereas the control linkers in FIGS. 4D and 4E show less effective overall binding and little gap selectivity.

FIGS. 5A to 5C depict the results from an ELISA testing of the 1e linker (SEQ ID NO:12) in the ZFP7264 background. FIG. 5A shows the results for the 1e linker, selected to skip a 1 bp gap between the module subsites. FIG. 5B shows the results for a standard flexible linker (TGGGGSQKP, SEQ ID NO:2), and FIG. 5C shows the results for a the flexible linker LRQKDERP (SEQ ID NO:3). ELISA scores are normalized to the parent, nonskipping ZFP7264 on its non-gapped target. "Gap sequence" is the identity of the skipped base(s) between the module subsites where (–) indicates the nongapped target. FIG. 5D shows an expanded version of the data from FIG. 5B where the ELISA score range is 0-0.6 as compared to 0-5 in the other panels.

FIG. 6, panels A through F, are graphs depicting gap selectivity for the linkers selected to skip 2 bp in ZFP8196. FIGS. 6A to 6E depict the results from an ELISA testing the linkers selected to skip a 2 by gap between the module subsites in the ZFP8196 background. FIGS. 6A through 6C show the results for the selected linkers 2f (SEQ ID NO:69), 2d (SEQ ID NO:70) and 2e (SEQ ID NO:71), whereas FIG. 6D shows the results for a previously published flexible linker (LRQKDGGGSERP (SEQ ID NO: 68)) and FIG. 6E shows the results for a standard flexible linker (TGGGGSGG GSQKP (SEQ ID NO: 14)). FIG. 6F shows an expanded version of the data shown in FIG. 6E where the ELISA score range is 0-0.1 as compared to 0-1 in the other panels. "Gap sequence" is the identity of the base(s) between the module subsites where (–) indicates the nongapped target. The selected linkers (FIGS. 6A-6C) demonstrate a clear preference for a 2 bp gap as compared to a 1 bp gap or no gap whereas the control linkers in FIGS. 6D and 6E show less effective overall binding and little gap selectivity.

FIG. 7, panels A and B, depict a summary of ELISA data from a study designed to analyze the portability of the 1 by skipping linkers to different ZFP backgrounds. Twelve different ZFPs were tested (indicated as ZFP1, ZFP2 etc.). FIG. 7A shows ELISA scores normalized to standard positive control ZFPs that have been shown to efficiently modify an endogenous IL2Rg locus when used as ZFNs (Urnov et al. (2005) Nature 435(7042):646-651). FIG. 7A discloses SEQ ID NOS 2, 12, 54, 56, and 55, respectively, in order of appearance. FIG. 7B shows all scores further normalized to each parent ZFP bearing the standard flexible linker TGGGGSQKP (SEQ ID NO:2). Underlined values in FIG. 7B indicate a >4-fold improvement in ELISA score for ZFPs with the selected linkers (1e (SEQ ID NO:12), if (SEQ ID NO:54), 1d (SEQ ID NO:56), and 1c (SEQ ID NO:55)) compared to the same host ZFP with the flexible linker TGGGGSQKP (SEQ ID NO:2). Overall, linkers 1e, 1f, 1d and 1c lead to a general increase in ELISA score of 3-5 fold over the flexible linker.

FIG. 8, panels A and B, depict a summary of ELISA data from a study designed to analyze the portability of the 2 by skipping linkers to different ZFP backgrounds. Six different ZFPs were tested (indicated as ZFP13, ZFP14 etc.). FIG. 8A shows ELISA scores normalized to standard positive control ZFPs that have been shown to efficiently modify an endogenous IL2Rg locus when used as ZFNs (Urnov et al. (2005) Nature 435(7042):646-651). FIG. 8A discloses SEQ ID NOS 14, 69, 70 and 71, respectively, in order of appearance. FIG. 8B shows all scores further normalized to each parent ZFP bearing the standard flexible linker TGGGGSGGGSQKP (SEQ ID NO:14). Underlined values in FIG. 8B indicate a >2-fold improvement in ELISA score for ZFPs with the selected linkers (2f (SEQ ID NO:69), 2d (SEQ ID NO:70) and 2e (SEQ ID NO:71)) compared to the same host ZFP with the flexible linker TGGGGSGGGSQKP (SEQ ID NO:14). Overall, linkers 2f (SEQ ID NO:69), 2d (SEQ ID NO:70) and 2e (SEQ ID NO:71) led to a general increase in ELISA score of 1.9-2.4 fold over the flexible linker.

FIGS. 9A and 9B depict example gels used to determine ZFN nuclease activity at endogenous loci by the CEL-I assay (measuring non-homologous end joining (NHEJ) activity, Surveyor™, Transkaryotic) to determine if linkers as described herein can be used in the context of different ZFNs. The gel shown in FIG. 9A depicts the results from the 1e (SEQ ID NO:12), 1f (SEQ ID NO:54), 1d (SEQ ID NO:56), and 1c (SEQ ID NO:55) linkers in the ZFN3 and ZFN4 backgrounds. The gel shown in FIG. 9B depicts the results from the 2f, 2d and 2e linkers (SEQ ID NOS 69-71, respectively) in the ZFN14 background. Percent gene modification by NHEJ, "Gene mod. (%)", is indicated at the bottom of the lanes. The negative control, "neg", is a sample transfected with a GFP bearing plasmid. The results from the ZFNs using a standard flexible linker (TGGGGSQKP (SEQ ID NO:2) for FIG. 9A and TGGGGSGGGSQKP (SEQ ID NO:14) for FIG. 9B) are shown in the lanes labeled "C". Unlabeled lanes contain samples of ZFNs bearing other linkers that were not further developed in these studies. The data in the gels demonstrates that the linkers as described herein significantly increase levels of gene modification as compared to the flexible linkers.

FIG. 10, panels A and B, depict a summary of gene modification studies for ZFNs as described above for FIG. 9 containing the indicated linkers selected to skip 1 bp. FIG. 10A is the quantitation of the percent gene modification for each ZFN with the set of five linkers tested (flexible (SEQ ID NO: 2), 1e (SEQ ID NO:12), 1f (SEQ ID NO:54), 1d (SEQ ID NO:56), and 1c (SEQ ID NO:55)). FIG. 10B shows this same data normalized to the flexible linker (TGGGGSQKP, SEQ ID NO:2) and also shows the average increase in gene modification across all the active ZFN pairs. Samples produced using high expression conditions (see Example 3) are highlighted in grey. ZFNs bearing exemplary linkers that improved the level of gene modification by >2-fold are underlined in FIG. 10B. Overall, ZFNs bearing linkers 1e (SEQ ID NO:12), 1f (SEQ ID NO:54), 1d (SEQ ID NO:56), and 1c (SEQ ID NO:55) lead to an average increase in gene modification of 1.8 to 2.8 fold over their respective host ZFNs bearing the flexible linker.

FIG. 11, panels A and B, depict a summary of gene modification studies as described for FIG. 9, for ZFNs containing the indicated linkers selected to skip a 2 bp gap between the module subsites of the 6 host ZFNs. FIG. 11A is the quantitation of the percent of gene modification for each ZFN with the set of four linkers tested (flexible (SEQ ID NO: 14), 2f (SEQ ID NO:69), 2d (SEQ ID NO:70) and 2e (SEQ ID NO:71)). FIG. 11B shows this same data normalized to the flexible linker (TGGGGSGGGSQKP, SEQ ID NO:14) and also shows the average increase across all the active ZFN pairs. Samples produced using high expression conditions (see Example 3) are highlighted in grey. ZFNs bearing exemplary linkers that improved the level of gene modification by >2-fold are underlined in FIG. 11B. ZFNs bearing linkers 2f (SEQ ID NO:69), 2d (SEQ ID NO:70) and 2e (SEQ ID NO:71) led to an average increase in gene modification of 1.5-2.0 fold over their respective host ZFNs bearing the flexible linker.

FIG. 13, panels A and B, depict the gap selectivity of the phage pool from the secondary selection for linkers spanning a 2-bp gap and the resulting amino acid sequences of the clones obtained in the selection. FIG. 13A shows the phage pool selected from the ZFP8196 library using a target with a 2 bp inserted gap (ATAAACTGdbCAAAAGGC (SEQ ID NO:34) (Table 2A)) tested for binding to each ZFP8196 target in Table 2C. Each test also included a control target for one other host ZFP to rule out nonspecific binding to DNA as well as a negative control sample which did not include a target site. The % of phage which successfully bound each target is indicated. The phage pool was from the sixth round of selection. Retention efficiency was determined essentially as previously described (Rebar, et al. *Methods in Enzymology,* 1996 (267):129-149). FIG. 13B shows amino acid sequences (SEQ ID NO:175 to 210) of linkers selected for skipping a 2 bp gap from the secondary selection in the context of ZFP8196. Selected linkers are enriched for proline and arginine (shaded).

DETAILED DESCRIPTION

Figure 4:
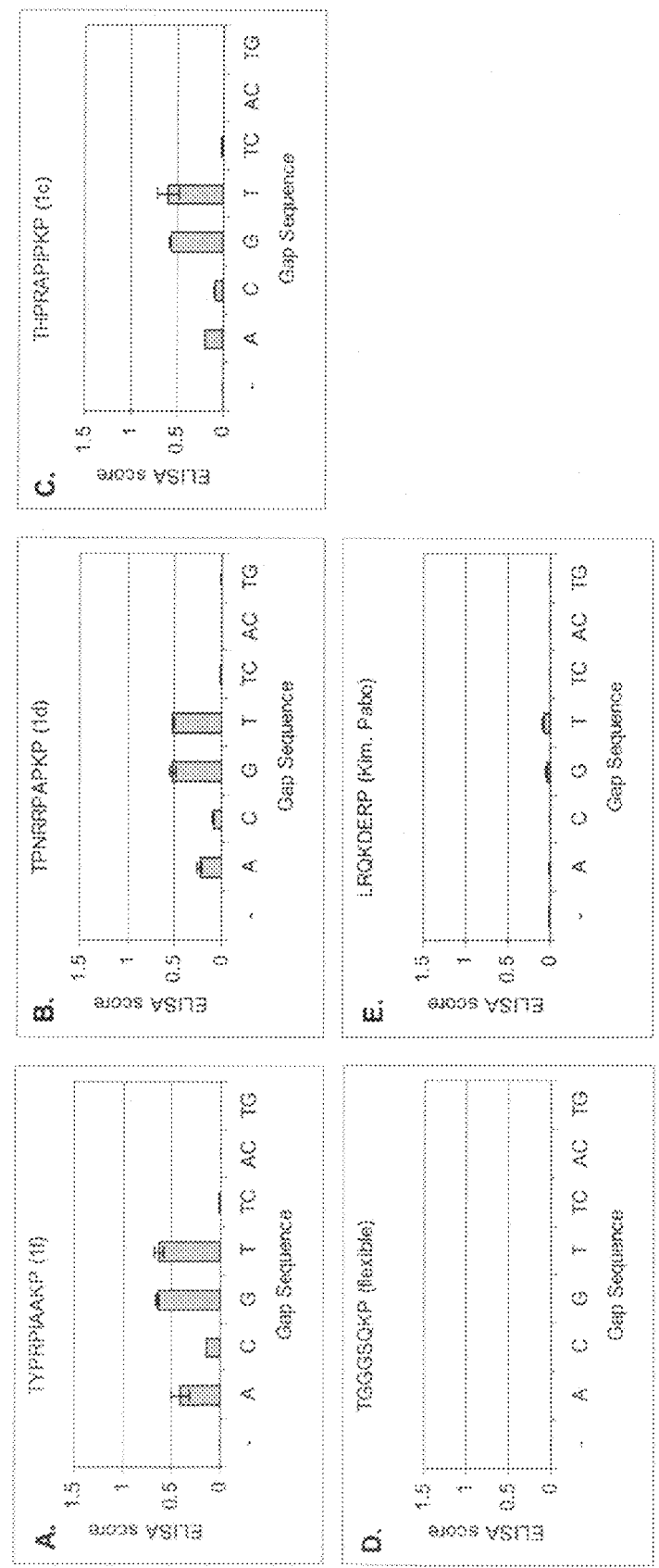
FIG. 4, panels A through E, are graphs depicting gap selectivity for linkers selected to skip 1 basepair in the zinc finger protein designated ZFP8196. In each panel, ELISA scores were normalized to the parent, non-skipping linker on its non-gapped target site. "Gap sequence" refers to the identity of the base(s) between the module subsites where (–) indicates the nongapped target.

Described herein are compositions for linking DNA-binding domains, particularly zinc-finger modules, to other zinc-finger modules. Unlike previously described linkers, the linkers described herein allow preferential and/or selective binding of targets bearing gaps between module subsites of 1 or 2 bp. The linkers are also capable of binding targets bearing 1, or 2 bp gaps at higher affinities than current linker designs. Exemplary linkers are shown in Tables 11 and 13. Thus, certain linkers described herein significantly increase the ability to design zinc-finger proteins which bind to specific target sites, thereby increasing the activity of fusion proteins (e.g., ZFP-TFs or ZFNs) comprising these linkers.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

DEFINITIONS

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acids.

A polypeptide is typically substantially identical to a second polypeptide, for example, where the two peptides differ only by conservative substitutions. A "conservative substitution," when describing a protein, refers to a change in the amino acid composition of the protein that does not substantially alter the protein's activity. Thus, "conservatively modified variations" of a particular amino acid sequence refers to amino acid substitutions of those amino acids that are not critical for protein activity or substitution of amino acids with other amino acids having similar properties (e.g., acidic, basic, positively or negatively charged, polar or non-polar, etc.) such that the substitutions of even critical amino acids do not substantially alter activity. Conservative substitution tables providing functionally similar amino acids are well known in the art. See, e.g., Creighton (1984) Proteins, W. H. Freeman and Company. In addition, individual substitutions, deletions or additions which alter, add or delete a single amino acid or a small percentage of amino acids in an encoded sequence are also "conservatively modified variations."

"Binding" refers to a sequence-specific, non-covalent interaction between macromolecules (e.g., between a protein and a nucleic acid). Not all components of a binding interaction need be sequence-specific (e.g., contacts with phosphate groups in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being defined by a lower $K_d$.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

Zinc finger binding domains (e.g., recognition regions of zinc fingers) can be "engineered" to bind to a predetermined nucleotide sequence. Non-limiting examples of methods for engineering zinc finger proteins are design and selection. A designed zinc finger protein is a protein not occurring in nature whose design/composition results principally from rational criteria. Rational criteria for design include application of substitution rules and computerized algorithms for processing information in a database storing information of existing ZFP designs and binding data. See, for example, U.S. Pat. Nos. 6,140,081; 6,453,242; and 6,534,261; see also WO 98/53058; WO 98/53059; WO 98/53060; WO 02/016536 and WO 03/016496.

A "selected" zinc finger protein is a protein not found in nature whose production results primarily from an empirical process such as phage display, interaction trap or hybrid selection. See e.g., U.S. Pat. No. 5,789,538; U.S. Pat. No. 5,925,523; U.S. Pat. No. 6,007,988; U.S. Pat. No. 6,013,453; U.S. Pat. No. 6,200,759; WO 95/19431; WO 96/06166; WO 98/53057; WO 98/54311; WO 00/27878; WO 01/60970 WO 01/88197 and WO 02/099084.

A "regulatory domain" or "functional domain" refers to a protein or a protein domain that has transcriptional modulation activity when tethered to a DNA binding domain, i.e., a ZFP. Typically, a regulatory domain is covalently or non-covalently linked to a ZFP (e.g., to form a fusion molecule) to effect transcription modulation. Regulatory domains can be activation domains or repression domains. Activation domains include, but are not limited to, VP16, VP64 and the p65 subunit of nuclear factor Kappa-B. Repression domains include, but are not limited to, KOX, KRAB MBD2B and v-ErbA. Additional regulatory domains include, e.g., transcription factors and co-factors (e.g., MAD, ERD, SID, early growth response factor 1, and nuclear hormone receptors), endonucleases, integrases, recombinases, methyltransferases, histone acetyltransferases, histone deacetylases etc. Activators and repressors include co-activators and co-repressors (see, e.g., Utley et al., Nature 394:498-502 (1998)). Alternatively, a ZFP can act alone, without a regulatory domain, to effect transcription modulation. Regulatory domains also can be nucleases, such as cleavage domains or cleavage half-domains.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left Cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain). See, also, U.S. Patent Publication No. 20050064474; and WO 2007/13989, incorporated herein by reference in their entireties.

"Chromatin" is the nucleoprotein structure comprising the cellular genome. Cellular chromatin comprises nucleic acid, primarily DNA, and protein, including histones and non-histone chromosomal protein. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

An "accessible region" is a site in cellular chromatin in which a target site present in the nucleic acid can be bound by an exogenous molecule which recognizes the target site. Without wishing to be bound by any particular theory, it is believed that an accessible region is one that is not packaged into a nucleosomal structure. The distinct structure of an accessible region can often be detected by its sensitivity to chemical and enzymatic probes, for example, nucleases.

A "target site" or "target sequence" is a nucleic acid sequence that defines a portion of a nucleic acid to which a binding molecule will bind, provided sufficient conditions for binding exist. For example, the sequence 5'-GAATTC-3' is a target site for the Eco RI restriction endonuclease.

A "module subsite" is a nucleic acid sequence that defines a portion of a nucleic acid to which a zinc-finger module (e.g. 1, 2, 3 or more zinc fingers) within a larger zinc-finger DNA binding protein will bind, provided sufficient conditions for binding exist.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule, a malfunctioning version of a normally-functioning endogenous molecule or an ortholog (functioning version of endogenous molecule from a different species).

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP DNA-binding domain and a cleavage domain) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression. Gene inactivation refers to any reduction in gene expression as compared to a cell that does not include a ZFP as described herein. Thus, gene inactivation may be partial or complete.

"Eukaryotic" cells include, but are not limited to, fungal cells (such as yeast), plant cells, animal cells, mammalian cells and human cells (e.g., T-cells).

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 20,000 nucleotide pairs in length, or any integral value of nucleotide pairs, or up to the length of a chromosome. A region is interest does not need to comprise only contiguous nucleic acid sequences.

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP DNA-binding domain is fused to a cleavage domain, the ZFP DNA-binding domain and the cleavage domain are in operative linkage if, in the fusion polypeptide, the ZFP DNA-binding domain portion is able to bind its target site and/or its binding site, while the cleavage domain is able to cleave DNA in the vicinity of the target site.

A "functional fragment" of a protein, polypeptide or nucleic acid is a protein, polypeptide or nucleic acid whose sequence is not identical to the full-length protein, polypeptide or nucleic acid, yet retains one or more of the functions of the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) *Nature* 340:245-246; U.S. Pat. No. 5,585,245 and PCT WO 98/44350.

Linkers

Described herein are amino acid sequences that fuse (link) DNA-binding modules (e.g., zinc-finger modules) to each other. The zinc-finger modules fused using the linkers described herein may contain 1, 2, 3, 4 or even more zinc fingers. In certain embodiments, the zinc-finger modules contain 1, 2, or 3 zinc fingers, which when linked together form a 3 or more finger zinc-finger protein.

The linker sequences described herein extend between the last residue of the α-helix in a zinc finger and the first residue of the β-sheet in the next zinc finger. The linker sequence therefore joins together two zinc fingers. Typically, the last (C-terminal) amino acid in a zinc finger is the C-terminal zinc-coordinating residue, whereas an aromatic residue (e.g., Phe) is typically the first amino acid of the following zinc finger. Accordingly, in a "wild type" zinc finger, threonine is the first residue in the linker, and proline is the last residue of the linker. Thus, for example, the canonical linker sequence for Zif268 is TG(E/Q)(K/R)P (SEQ ID NO:129). See, e.g., U.S. Pat. Nos. 6,479,626; 6,903,185 and 7,153,949.

Additional linkers are described for example in U.S. Patent Publication 20030119023, which describes linkers including multiple glycine residues (e.g., TGGGGSQKP (SEQ ID NO:2), TGGGGSGGGSQKP (SEQ ID NO:14) and TGGGGSGGSGGSQKP (SEQ ID NO:15), TGGEKP (SEQ ID NO:16), TGGQKP (SEQ ID NO:17), TGGSGEKP (SEQ ID NO:18), TGGSGQKP (SEQ ID NO:19), TGGSGGS-GEKP (SEQ ID NO:20), and TGGSGGSGQKP (SEQ ID NO:21).

Typically, the linkers are made using recombinant nucleic acids encoding the linker and the nucleic acid binding modules, which are fused via the linker amino acid sequence. The linkers may also be made using peptide synthesis and then linked to the nucleic acid binding modules. Methods of manipulating nucleic acids and peptide synthesis methods are known in the art (see, for example, Maniatis, et al., 1991. *Molecular Cloning: A Laboratory Manual*. Cold Spring Harbor, N.Y., Cold Spring Harbor Laboratory Press).

The linkers described herein are more rigid than the linkers previously used, and allow efficient binding of each zinc finger module to its target site only when subsites are separated by a specific number of base pairs.

Thus, unlike previous linkers, the linkers described herein include at least one internal or N-terminal proline residue, namely a proline residue not at the C-terminal of the linker. The linkers described herein have the following general amino acid structure:

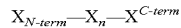

$X_{N\text{-}term}$—$X_n$—$X^{C\text{-}term}$ where X is any amino acid residue, $X_n$ comprises at least 3 amino acid residues and at least one of $X^{N\text{-}term}$ and $X_n$ comprises a proline residue. Non-limiting examples of such linkers are shown in Tables 4, 5, 6, 9, 10, 11 or 13. Furthermore, the linkers described herein also typically include at least two basic residues, for example one or more arginine residues, one or more histidine residues, one or more lysine residues or combinations thereof.

The linkers of the invention can be any length, typically 5 or more amino acids in length. In certain embodiments, the linkers are 5, 6, 7, 8, 9, 10, 11, 12, 13, 14, 15, 16, 17, 18, 19, 20 or even more amino acids length.

DNA-Binding Modules

The linker sequences described herein are advantageously used to link DNA-binding modules.

Any DNA-binding domain can be used in the methods disclosed herein. In certain embodiments, the DNA binding domain comprises a zinc-finger protein. Preferably, the zinc-finger protein is non-naturally occurring in that it is engineered to bind to a target site of choice. See, for example, Beerli et al., (2002) *Nature Biotechnol.* 20:135-141; Pabo et al. (2001) *Ann. Rev. Biochem.* 70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.* 10:411-416. An engineered zinc-finger binding domain can have a novel binding specificity, compared to a naturally-occurring zinc-finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in co-owned WO 02/077227.

Selection of target sites; ZFPs and methods for design and construction of fusion proteins (and polynucleotides encoding same) are known to those of skill in the art and described in detail in U.S. Patent Application Publication Nos. 20050064474 and 20060188987, incorporated by reference in their entireties herein.

In addition, as disclosed in these and other references, zinc-finger domains and/or multi-finger zinc-finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

Alternatively, the DNA-binding domain may be derived from a nuclease. For example, the recognition sequences of homing endonucleases and meganucleases such as I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII are known. See also U.S. Pat. No. 5,420,032; U.S. Pat. No. 6,833,252; Belfort et al. (1997) *Nucleic Acids Res.* 25:3379-3388; Dujon et al. (1989) *Gene* 82:115-118; Perler et al. (1994) *Nucleic Acids Res.* 22, 1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue. In addition, the DNA-binding specificity of homing endonucleases and meganucleases can be engineered to bind non-natural target sites. See, for example, Chevalier et al. (2002) *Molec. Cell* 10:895-905; Epinat et al. (2003) *Nucleic Acids Res.* 31:2952-2962; Ashworth et al. (2006) *Nature* 441:656-659; Paques et al. (2007) *Current Gene Therapy* 7:49-66; U.S. Patent Publication No. 20070117128.

In some embodiments, the DNA binding domain is an engineered domain from a TAL effector (TALE) derived from the plant pathogen *Xanthomonas* (see, Miller et al. (2010) *Nature Biotechnology*, December 22 [Epub ahead of print]; Boch et al, (2009) *Science* 29 Oct. 2009 (10.1126/science.117881) and Moscou and Bogdanove, (2009) *Science* 29 Oct. 2009 (10.1126/science.1178817); see, also, U.S. Provisional Application Nos. 61/395,836, filed May 17, 2010; 61/409,421, filed Aug. 21, 2010; 61/45,121, filed Oct. 13, 2010; 61/459,891, filed Dec. 20, 2010; Application No. 61/462,482, filed Feb. 2, 2011; Application No. 61/465,869, filed Mar. 24, 2011, the disclosures of which are hereby incorporated by reference in their entireties.

Regulatory Domains

Zinc-finger modules linked as described herein are often expressed with an exogenous domain (or functional fragment thereof) as fusion proteins. Common regulatory domains for addition to the ZFP include, e.g., transcription factor domains (activators, repressors, co-activators, co-repressors), silencers, oncogenes (e.g., myc, jun, fos, myb, max, mad, rel, ets, bcl, myb, mos family members etc.); DNA repair enzymes and their associated factors and modifiers; DNA rearrangement enzymes and their associated factors and modifiers; chromatin associated proteins and their modifiers (e.g. kinases, acetylases and deacetylases); and DNA modifying enzymes (e.g., methyltransferases, topoisomerases, helicases, ligases, kinases, phosphatases, polymerases, endonucleases) and their associated factors and modifiers.

An exemplary functional domain for fusing with a DNA-binding domain such as, for example, a ZFP, to be used for repressing expression of a gene is a KRAB repression domain from the human KOX-1 protein (see, e.g., Thiesen et al., *New Biologist* 2, 363-374 (1990); Margolin et al., *Proc. Natl. Acad. Sci.* USA 91, 4509-4513 (1994); Pengue et al., *Nucl. Acids Res.* 22:2908-2914 (1994); Witzgall et al., *Proc. Natl. Acad. Sci.* USA 91, 4514-4518 (1994). Another suitable repression domain is methyl binding domain protein 2B (MBD-2B) (see, also Hendrich et al. (1999) *Mamm. Genome* 10:906-912 for description of MBD proteins). Another useful repression domain is that associated with the v-ErbA protein. See, for example, Damm, et al. (1989) *Nature* 339:593-597; Evans (1989) *Int. J. Cancer Suppl.* 4:26-28; Pain et al. (1990) *New Biol.* 2:284-294; Sap et al. (1989) *Nature* 340:242-244; Zenke et al. (1988) *Cell* 52:107-119; and Zenke et al. (1990) *Cell* 61:1035-1049.

Additional exemplary repression domains include, but are not limited to, KRAB (also referred to as "KOX"), SID, MBD2, MBD3, members of the DNMT family (e.g., DNMT1, DNMT3A, DNMT3B), Rb, and MeCP2. See, for example, Bird et al. (1999) *Cell* 99:451-454; Tyler et al. (1999) *Cell* 99:443-446; Knoepfler et al. (1999) *Cell* 99:447-450; and Robertson et al. (2000) *Nature Genet.* 25:338-342. Additional exemplary repression domains include, but are not limited to, ROM2 and AtHD2A. See, for example, Chem et al. (1996) *Plant Cell* 8:305-321; and Wu et al. (2000) *Plant J.* 22:19-27.

Suitable domains for achieving activation include the HSV VP16 activation domain (see, e.g., Hagmann et al., *J. Virol.* 71, 5952-5962 (1997)) nuclear hormone receptors (see, e.g., Torchia et al., *Curr. Opin. Cell. Biol.* 10:373-383 (1998)); the p65 subunit of nuclear factor kappa B (Bitko and Barik, *J. Virol.* 72:5610-5618 (1998) and Doyle and Hunt, *Neuroreport* 8:2937-2942 (1997)); Liu et al., *Cancer Gene Ther.* 5:3-28 (1998)), or artificial chimeric functional domains such as VP64 (Seifpal et al., *EMBO J.* 11, 4961-4968 (1992)). Additional exemplary activation domains include, but are not limited to, VP16, VP64, p 300, CBP, PCAF, SRC1 PvALF, AtHD2A and ERF-2. See, for example, Robyr et al. (2000) *Mol. Endocrinol.* 14:329-347; Collingwood et al. (1999) *J. Mol. Endocrinol.* 23:255-275; Leo et al. (2000) *Gene* 245:1-11; Manteuffel-Cymborowska (1999) *Acta Biochim. Pol.* 46:77-89; McKenna et al. (1999) *J. Steroid Biochem. Mol. Biol.* 69:3-12; Malik et al. (2000) *Trends Biochem. Sci.* 25:277-283; and Lemon et al. (1999) *Curr. Opin. Genet. Dev.* 9:499-504. Additional exemplary activation domains include, but are not limited to, OsGAI, HALF-1, C1, AP1, ARF-5, -6, -7, and -8, CPRF1, CPRF4, MYC-RP/GP, and TRAB1. See, for example, Ogawa et al. (2000) *Gene* 245:21-29; Okanami et al. (1996) *Genes Cells* 1:87-99; Goff et al. (1991) *Genes Dev.* 5:298-309; Cho et al. (1999) *Plant Mol. Biol.* 40:419-429; Ulmason et al. (1999) *Proc. Natl. Acad. Sci. USA* 96:5844-5849; Sprenger-Haussels et al. (2000) *Plant J.* 22:1-8; Gong et al. (1999) *Plant Mol. Biol.* 41:33-44; and Hobo et al. (1999) *Proc. Natl. Acad. Sci. USA* 96:15,348-15,353.

In certain embodiments, the regulatory domain comprises a nuclease (e.g., cleavage domain). Such engineered nucleases can be used to create a double-strand break (DSB) in a target nucleotide sequence, which increases the frequency of donor nucleic acid introduction via homologous recombination at the targeted locus (targeted integration) more than 1000-fold. In addition, the inaccurate repair of a site-specific DSB by non-homologous end joining (NHEJ) can also result in gene disruption. Nucleases can be used for a wide variety of purposes such as for cell line engineering as well as for therapeutic applications.

Cleavage domains of the fusion proteins disclosed herein can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) *Nucleic Acids Res.* 25:3379-3388. Additional enzymes which cleave DNA are known (e.g., S1 Nuclease; mung bean nuclease; pancreatic DNase I; micrococcal nuclease; yeast HO endonuclease; see also Linn et al. (eds.) *Nucleases*, Cold Spring Harbor Laboratory Press, 1993). One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof).

In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994a) *Proc. Natl. Acad. Sci. USA* 91:883-887; Kim et al. (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer. Bitinaite et al. (1998) *Proc. Natl. Acad. Sci. USA* 95: 10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using zinc finger-Fok I fusions, two fusion proteins, each comprising a FokI cleavage half-domain, can be used to reconstitute a catalytically active cleavage domain. Alternatively, a single polypeptide molecule containing a zinc finger binding domain and two Fok I cleavage half-domains can also be used. Parameters for targeted cleavage and targeted sequence alteration using zinc finger-Fok I fusions are provided elsewhere in this disclosure.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in International Publication WO 07/014,275, incorporated herein in its entirety. Additional restriction enzymes also contain separable binding and cleavage domains, and these are contemplated by the present disclosure. See, for example, Roberts et al. (2003) *Nucleic Acids Res.* 31:418-420.

In certain embodiments, the cleavage domain comprises one or more engineered cleavage half-domain (also referred to as dimerization domain mutants) that minimize or prevent homodimerization, as described, for example, in U.S. Patent Publication Nos. 20050064474 and 20060188987 and in U.S. application Ser. No. 11/805,850 (filed May 23, 2007), the disclosures of all of which are incorporated by reference in their entireties herein. Amino acid residues at positions 446, 447, 479, 483, 484, 486, 487, 490, 491, 496, 498, 499, 500, 531, 534, 537, and 538 of Fok I are all targets for influencing dimerization of the Fok I cleavage half-domains.

Exemplary engineered cleavage half-domains of Fok I that form obligate heterodimers include a pair in which a first cleavage half-domain includes mutations at amino acid residues at positions 490 and 538 of Fok I and a second cleavage half-domain includes mutations at amino acid residues 486 and 499.

Thus, in one embodiment, a mutation at 490 replaces Glu (E) with Lys (K); the mutation at 538 replaces Iso (I) with Lys (K); the mutation at 486 replaced Gln (Q) with Glu (E); and the mutation at position 499 replaces Iso (I) with Lys (K). Specifically, the engineered cleavage half-domains described herein were prepared by mutating positions 490 (E→K) and 538 (I→K) in one cleavage half-domain to produce an engineered cleavage half-domain designated "E490K:I538K" and by mutating positions 486 (Q→E) and 499 (I→L) in another cleavage half-domain to produce an engineered cleavage half-domain designated "Q486E:I499L". The engineered cleavage half-domains described herein are obligate heterodimer mutants in which aberrant cleavage is minimized or abolished. See, e.g., Example 1 of WO 07/139,898. In certain embodiments, the engineered cleavage half-domain comprises mutations at positions 486, 499 and 496 (numbered relative to wild-type FokI), for instance mutations that replace the wild type Gln (Q) residue at position 486 with a Glu (E) residue, the wild type Iso (I) residue at position 499 with a Leu (L) residue and the wild-type Asn (N) residue at position 496 with an Asp (D) or Glu (E) residue (also referred to as a "ELD" and "ELE" domains, respectively). In other embodiments, the engineered cleavage half-domain comprises mutations at positions 490, 538 and 537 (numbered relative to wild-type FokI), for instance mutations that replace the wild type Glu (E) residue at position 490 with a Lys (K) residue, the wild type Iso (I) residue at position 538 with a Lys (K) residue, and the wild-type His (H) residue at position 537 with a Lys (K) residue or a Arg (R) residue (also referred to as "KKK" and "KKR" domains, respectively). In other embodiments, the engineered cleavage half-domain comprises mutations at positions 490 and 537 (numbered relative to wild-type FokI), for instance mutations that replace the wild type Glu (E) residue at position 490 with a Lys (K) residue and the wild-type His (H) residue at position 537 with a Lys (K) residue or a Arg (R) residue (also referred to as "KIK" and "KIR" domains, respectively). (See U.S. patent application Ser. No. 12/931,660).

Engineered cleavage half-domains described herein can be prepared using any suitable method, for example, by site-directed mutagenesis of wild-type cleavage half-domains (Fok I) as described in U.S. Patent Publication No. 20050064474 (see, e.g., Example 5); and WO 07/139,898.

Alternatively, nucleases may be assembled in vivo at the nucleic acid target site using so-called "split-enzyme" technology (see e.g. U.S. Patent Publication No. 20090068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain.

Fusion molecules are constructed by methods of cloning and biochemical conjugation that are well known to those of skill in the art. Fusion molecules comprise a DNA-binding domain and a functional domain (e.g., a transcriptional activation or repression domain). Fusion molecules also optionally comprise nuclear localization signals (such as, for example, that from the SV40 medium T-antigen) and epitope tags (such as, for example, FLAG and hemagglutinin). Fusion proteins (and nucleic acids encoding them) are designed such that the translational reading frame is preserved among the components of the fusion.

For such applications, the fusion molecule is typically formulated with a pharmaceutically acceptable carrier, as is known to those of skill in the art. See, for example, Remington's Pharmaceutical Sciences, 17th ed., 1985; and co-owned WO 00/42219.

Kits

Also provided are kits comprising any of the linkers described herein and/or for performing any of the above methods. The kits typically contain a linker sequence as described herein (or a polynucleotide encoding a linker as described herein). The kit may supply the linker alone or may provide vectors into which a DNA-binding domain and/or nuclease of choice can be readily inserted into. The kits can also contain cells, buffers for transformation of cells, culture media for cells, and/or buffers for performing assays. Typically, the kits also contain a label which includes any material such as instructions, packaging or advertising leaflet that is attached to or otherwise accompanies the other components of the kit.

Applications

The disclosed linkers are advantageously used to enhance the repertoire of target sites for engineered zinc-finger proteins. For example, the linkers described herein facilitate binding to desired target sites when the module subsites are not adjacent. Thus, there would effectively be an increase the number of ZFPs that could be constructed to target a given nucleic acid sequence for a given repertoire size. Furthermore, because the linkers described distinguish between various module subsite separations (e.g., 0, 1 and 2 base pair gaps), they reduce binding of ZFPs to improper target sites. For example, a ZFP with a flexible linker designed to skip 2 basepairs (e.g. TGGGGSGGGSQKP (SEQ ID NO:14)) is able to bind to target sites with either 0, 1, or 2 basepairs between the module subsites. This same ZFP with a 2 bp-skipping linker as described herein should bind well to a target with 2 basepairs between the module subsites, but should not be able to bind efficiently to targets with 0 or 1 basepairs between module subsites (improper or unintended target sites).

Thus, linkers described herein can be used in any application for which zinc-finger proteins are currently used, including, but not limited to zinc-finger transcription factors (ZFP-TFs) for modulation of gene expression and/or in zinc-finger nucleases (ZFNs) for cleavage. See, e.g., U.S. Pat. Nos. 6,534,261; 6,599,692; 6,689,558; 7,067,317; 7,262,054 and 7,253,273; U.S. Patent Publication Nos. 20050064474; 2006/0063231; 2007/0134796; 2007/0218528; 2008/0015164; 2008/0188000; 2008/0299580 and 2008/0159996, incorporated by reference in their entireties herein.

Accordingly, the disclosed linkers can be used in any ZFP or ZFN for any method in which specifically targeted modulation or cleavage is desirable. For example, ZFP-TFs and ZFNs can be used to treat genetic diseases, infections (viral or bacterial), to generate cell lines, animals and or plants in which desired genes are activated, repressed, targeted by homologous recombination and/or knocked-in or out. Accordingly, the linkers described herein can also be used to more efficiently clone DNA and in genome modifications facilitated by ZFNs, which is broadly applicable in many areas of biotechnology and basic science.

EXAMPLES

Example 1

Selection of Linkers

Linker selections were performed in the context of three different host ZFPs: "ZFP7263", "ZFP7264" and "ZFP8196"

(see U.S. Patent Publication Nos. 20050064474 for 7263 and 7264 and 20080159996 for 8196), which each contained four fingers. Recognition helices of each finger for each host ZFP are provided in Table 1, while the full sequence of each host ZFP is provided in FIG. 1A. Selections were carried out as follows: (i) first, a library was generated within each host ZFP that replaced codons in the central linker with a mixture of two to twelve fully randomized codons (FIG. 1B); Sequencing of naïve libraries showed good diversity of sequences with no clone represented more than once; (ii) next, the libraries were expressed on the surface of filamentous bacteriophage; (iii) phage-expressed ZFP libraries were then selected for binding to biotinylated target variants that contained a 1- or 2-bp insertion at the center of the host protein binding site (i.e. in the region spanned by the randomized linker) (Table 2A). Each insertion comprised a gap between the binding sequences for the second and third fingers of the host protein that must be bridged by a longer linker to enable efficient binding (Table 2A). Insertions consisted of a mixture of bases in order to favor the selection of linkers with no intrinsic base specificity. Five selection cycles were performed. During the final four cycles, a counterselection was employed with a 1000-fold molar excess of binding sites that were nonbiotinylated and that contained non-targeted gap lengths (i.e. if phage were selected using a target sequence with a 1 bp gap length, the counterselection comprised targets with 0, 2, 3 and 4 bp gaps; if phage were selected using a target sequence with a 2 bp gap length, the counterselection comprised targets with 0, 1 and 3 and 4 bp gaps—see Table 2B).

Phage pools from the fifth round of selection were screened for the ability to selectively bind sequences bearing the targeted gap length, and these studies revealed gap selective binding (FIG. 2). In particular, phage pools selected to skip a 1 bp gap in the context of ZFP8196 showed a 25-fold preference for targets bearing a 1 bp gap as compared to no gap. Phage pools selected to skip a 1 bp gap in the context of ZFP7263 showed a 26-fold preference for targets bearing a 1 bp gap as compared to no gap. Phage pools selected to skip a 1 bp gap in the context of ZFP7264 showed a 5.5 fold preference targets bearing a 1 bp gap as compared to no gap. Each of these pools also exhibited little or no binding to targets bearing longer gap lengths (2, 3 or 4 bp).

Phage pools selected to skip a 2 bp gap in the context of ZFP8196 showed a 7-fold preference for targets bearing 2 bp gap as compared to a 1 bp gap as well as a >30-fold preference over targets bearing 0, 3 and 4 bp gaps.

TABLE 1

Host ZFP recognition helices

| ZFP | Finger 1 | Finger 2 | Finger 3 | Finger 4 |
|---|---|---|---|---|
| 8196 | RSDNLSV (SEQ ID NO: 22) | QKINLQV (SEQ ID NO: 23) | RSDVLSE (SEQ ID NO: 24) | QRNHRTT (SEQ ID NO: 25) |
| 7264 | RSDTLSE (SEQ ID NO: 26) | ARSTRTT (SEQ ID NO: 27) | RSDSLSK (SEQ ID NO: 28) | QRSNLKV (SEQ ID NO: 29) |
| 7263 | RSDNLSV (SEQ ID NO: 22) | RNAHRIN (SEQ ID NO: 30) | RSDTLSE (SEQ ID NO: 26) | ARSTRTN (SEQ ID NO: 31) |

TABLE 2A

Target sites used for selection

| ZFP w/randomized linker | Target sites |
|---|---|
| 8196 | ATAAACTGdCAAAAGGC (SEQ ID NO: 33) |
|  | ATAAACTGdbCAAAAGGC (SEQ ID NO: 34) |
| 7264 | TTAAAGCGhGCTCCGAA (SEQ ID NO: 38) |
|  | TTAAAGCGhdGCTCCGAA (SEQ ID NO: 39) |
| 7263 | CCACTCTGhTGGAAGTG (SEQ ID NO: 43) |
|  | CCACTCTGhhTGGAAGTG (SEQ ID NO: 44) |

Table 2A. Target sites used for selections. Duplex DNA target sites used in phage studies had the general form of: TATAAT $(X)_{17-18}TTCACAGTCAGTCCACACGTC$, (SEQ ID NO: 67) where $(X)_{17-18}$ was replaced with sequences listed in the table. DNA duplexes were made by extending a primer that annealed to the italicized sequence and which was biotinylated at its 5' end. Underlined bases indicate the binding sequences for the four fingers of each host ZFP, while lowercase bases indicate inserted nucleotides (or "gap" bases) that must be spanned by the selected linkers. Degeneracy codes for gap bases are as follows: "d" denotes a mix of A, G, and T; "b" denotes a mix of C, G, and T; "h" denotes a mix of A, C, and T; and "v" denotes a mix of A, C, and G.

TABLE 2B

Competitor sites used during selection

| ZFP w/randomized linker | Competitor sites |
|---|---|
| 8196 | ATAAACTGCAAAAGGC (SEQ ID NO: 32) |
|  | ATAAACTGdCAAAAGGC (SEQ ID NO: 33) |
|  | ATAAACTGdbCAAAAGGC (SEQ ID NO: 34) |
|  | ATAAACTGdbbCAAAAGGC (SEQ ID NO: 35) |
|  | ATAAACTGdbbbCAAAAGGC (SEQ ID NO: 36) |
| 7264 | TTAAAGCGGCTCCGAA (SEQ ID NO: 37) |
|  | TTAAAGCGhGCTCCGAA (SEQ ID NO: 38) |
|  | TTAAAGCGhdGCTCCGAA (SEQ ID NO: 39) |
|  | TTAAAGCGhdvGCTCCGAA (SEQ ID NO: 40) |
|  | TTAAAGCGhdvdGCTCCGAA (SEQ ID NO: 41) |
| 7263 | CCACTCTGTGGAAGTG (SEQ ID NO: 42) |
|  | CCACTCTGhTGGAAGTG (SEQ ID NO: 43) |
|  | CCACTCTGhhTGGAAGTG (SEQ ID NO: 44) |

TABLE 2B-continued

Competitor sites used during selection

| ZFP w/randomized linker | Competitor sites |
|---|---|
| | CCACTCTGhhhTGGAAGTG (SEQ ID NO: 45) |
| | CCACTCTGhhhbTGGAAGTG (SEQ ID NO: 46) |

Table 2B. Competitor sites used during selections. Duplex DNA competitor sites had the general form of: TATAAT(X)$_{16-20}$TTCACAGTCAGTCCACACGTC, (SEQ ID NO: 5) where (X)$_{16-20}$ was replaced with sequences listed in the table. DNA duplexes were made by extending a (non-biotinylated) primer that annealed to the italicized sequence. Underlined bases indicate the binding sequences for the four fingers of each host ZFP, while lowercase bases indicate inserted nucleotides (or "gap" bases). Degeneracy codes for gap bases are as follows: "d" denotes a mix of A, G, and T; "b" denotes a mix of C, G, and T; "h" denotes a mix of A, C, and T; and "v" denotes a mix of A, C, and G.

TABLE 2C

Targets used for phage pool gap selectivity studies

| ZFP w/randomized linker | Gap | Target sites |
|---|---|---|
| 8196 | 0 gap | ATAAACTGCAAAAGGC (SEQ ID NO: 32) |
| | 1 gap | ATAAACTGdCAAAAGGC (SEQ ID NO: 33) |
| | 2 gap | ATAAACTGdbCAAAAGGC (SEQ ID NO: 34) |
| | 3 gap | ATAAACTGdbbCAAAAGGC (SEQ ID NO: 35) |
| | 4 gap | ATAAACTGdbbbCAAAAGGC (SEQ ID NO: 36) |
| 7264 | 0 gap | TTAAAGCGGCTCCGAA (SEQ ID NO: 37) |
| | 1 gap | TTAAAGCGhGCTCCGAA (SEQ ID NO: 38) |
| | 2 gap | TTAAAGCGhdGCTCCGAA (SEQ ID NO: 39) |
| | 3 gap | TTAAAGCGhdvGCTCCGAA (SEQ ID NO: 40) |
| | 4 gap | TTAAAGCGhdvdGCTCCGAA (SEQ ID NO: 41) |
| 7263 | 0 gap | CCACTCTGTGGAAGTG (SEQ ID NO: 42) |
| | 1 gap | CCACTCTGhTGGAAGTG (SEQ ID NO: 43) |
| | 2 gap | CCACTCTGhhTGGAAGTG (SEQ ID NO: 44) |
| | 3 gap | CCACTCTGhhhTGGAAGTG (SEQ ID NO: 45) |
| | 4 gap | CCACTCTGhhhbTGGAAGTG (SEQ ID NO: 46) |

Table 2C. Targets used for phage pool gap selectivity studies. Duplex DNA sites used in phage pool gap selectivity studies had the general form of: TATAAT(X)$_{16-20}$TTCACAGTCAGTCCACACGTC, (SEQ ID NO: 5) where (X)$_{16-20}$ was replaced with sequences listed in the table. DNA duplexes were made by extending a biotinylated primer that annealed to the italicized sequence. Underlined bases indicate the binding sequences for the four fingers of each host ZFP, while lowercase bases indicate inserted nucleotides (or "gap" bases). Degeneracy codes for gap bases are as follows: "d" denotes a mix of A, G, and T; "b" denotes a mix of C, G, and T; "h" denotes a mix of A, C, and T; and "v" denotes a mix of A, C, and G.

Sequencing

Genes encoding the selected ZFPs were subcloned and sequenced. FIG. 3A presents linkers selected for skipping 1 bp gaps in the context of all three host proteins, while FIG. 3B shows linkers selected for skipping 2 bp in the context of the "ZFP8196" host. The sequencing results revealed a strong compositional bias in the selected linkers towards proline- and arginine-rich sequences. Clear linker length trends were also apparent: although the starting libraries encoded approximately equal proportions of 11 different linker lengths (2-12 residues), selected linkers featured narrower distributions of from 5-8 residues (for the 1 bp gap) or 9-11 residues (for the 2 bp gap).

Example 2

Initial Characterization of Selected ZFPs

As an initial functional assessment of the linkers selected to skip 1 bp, ZFPs bearing the linkers listed in FIG. 3A were subcloned, expressed as free protein using an in vitro transcription-translation kit, and evaluated by ELISA for binding to targets bearing insertions of 0, 1 or 2 bp opposite the selected linker. Targets for these studies are listed in Table 3. Nine additional control proteins were generated by replacing the central linker of each host ZFP with three alternative, previously characterized, linker sequences which collectively represented the state of the art for spanning 1 bp. The sequences of these control linkers were LRQKDERP (SEQ ID NO:3) (see, U.S. Pat. No. 6,479,626), TGEGGKP (SEQ ID NO:48), TGGGGSQKP (SEQ ID NO:2). These control proteins, as well as the host ZFPs, were also included in the ELISA studies.

Table 3 shows the targets used for ELISA studies of ZFPs selected to skip a 1 bp gap. Duplex DNA sites used these studies had the general form TTAG(X)$_{16-18}$TATC, (SEQ ID NO:94) where (X)$_{16-18}$ was replaced with sequences listed in the table. Each duplex DNA target was made by annealing a complementary oligonucleotide bearing a biotin at its 5' end. Underlines indicate the binding sequences for the four fingers of each host ZFP, while lowercase letters indicate inserted nucleotides (or "gap" bases).

The results of these studies are provided in Tables 4, 5 and 6, with each table listing data for proteins derived from a different host ZFP. Table 4 provides data for ZFP8196-derived proteins; Table 5 provides data for ZFP7263-derived proteins; and Table 6 provides data for ZFP7264-derived proteins. In each table, binding data for the host ZFP is listed in the top row, followed by binding data for three control proteins in rows 2-4, followed by data for the ZFPs selected from the phage display libraries. The values are normalized to the ELISA signal obtained from the binding of the parent ZFP to its unmodified target.

Each set of proteins exhibited a similar pattern of binding behavior, in three key respects: First, each parent ZFP bound well to its unmodified target (the "0-bp gap" target in Tables 4, 5 and 6) but not to any variant bearing inserts of 1 or 2 hp. This was expected since the parental linkers (either TGEKP (SEQ ID NO:1) (for ZFP8196) or TGSQKP (SEQ ID NO:72) (for ZFP7263 and ZFP7264)) are too short to span any additional inserted base.

Second, in almost all cases the control proteins bound very poorly to targets with a 1 bp insert (normalized ELISA values were 0.10 or less for 31 of 36 such measurements). This indicates the poor performance of the linkers available prior to these studies. Moreover, the linkers used by these proteins showed no consistent preference for targets bearing a 1 bp insert (vs a 0 bp insert).

Third, in contrast to the behavior of the control proteins, the phage-selected ZFPs bound with much higher affinity to targets bearing a 1 bp insert as well as with a much higher level of discrimination against binding targets containing no inserted base. These proteins were also very selective for binding targets with a 1 bp insert vs targets bearing a 2 bp insert.

TABLE 3

Targets used for ELISA studies of ZFPs selected to skip a 1 bp gap

| ZFP w/randomized linker | Gap Sequence | Target sites |
|---|---|---|
| 8196 | — | ATAAACTGCAAAAGGC (SEQ ID NO: 32) |
| | A | ATAAACTGaCAAAAGGC (SEQ ID NO: 73) |
| | C | ATAAACTGcCAAAAGGC (SEQ ID NO: 74) |
| | G | ATAAACTGgCAAAAGGC (SEQ ID NO: 75) |
| | T | ATAAACTGtCAAAAGGC (SEQ ID NO: 76) |
| | TC | ATAAACTGtcCAAAAGGC (SEQ ID NO: 77) |
| | AC | ATAAACTGacCAAAAGGC (SEQ ID NO: 78) |

TABLE 3-continued

Targets used for ELISA studies of ZFPs selected to skip a 1 bp gap

| ZFP w/randomized linker | Gap Sequence | Target sites |
|---|---|---|
| | TG | ATAAACTGtgCAAAAGGC (SEQ ID NO: 79) |
| 7264 | — | TTAAAGCGGCTCCGAA (SEQ ID NO: 37) |
| | A | TTAAAGCGaGCTCCGAA (SEQ ID NO: 80) |
| | C | TTAAAGCGcGCTCCGAA (SEQ ID NO: 81) |
| | G | TTAAAGCGgGCTCCGAA (SEQ ID NO: 82) |
| | T | TTAAAGCGtGCTCCGAA (SEQ ID NO: 83) |
| | TT | TTAAAGCGttGCTCCGAA (SEQ ID NO: 84) |
| | TA | TTAAAGCGtaGCTCCGAA (SEQ ID NO: 85) |
| | CT | TTAAAGCGctGCTCCGAA (SEQ ID NO: 86) |
| 7263 | — | CCACTCTGTGGAAGTG (SEQ ID NO: 42) |
| | A | CCACTCTGaTGGAAGTG (SEQ ID NO: 87) |
| | C | CCACTCTGcTGGAAGTG (SEQ ID NO: 88) |
| | G | CCACTCTGgTGGAAGTG (SEQ ID NO: 89) |
| | T | CCACTCTGtTGGAAGTG (SEQ ID NO: 90) |
| | AC | CCACTCTGacTGGAAGTG (SEQ ID NO: 91) |
| | AT | CCACTCTGatTGGAAGTG (SEQ ID NO: 92) |
| | CT | CCACTCTGctTGGAAGTG (SEQ ID NO: 93) |

TABLE 4

ELISA results for variants of the ZFP "8196" with different center linkers

ELISA score for binding to targets having the indicated gap [score is normalized to 8196 bound to its non-gapped target (underlined entry)]

| Sequence of the center linker | 0-bp gap | 1-bp gap | | | | average ratio of 1 bp:0 bp score | 2-bp gap | | |
|---|---|---|---|---|---|---|---|---|---|
| | — | A | C | G | T | | TC | AC | TG |
| TGEKP (SEQ ID NO: 1) | 1.00 | 0.01 | 0.01 | 0.03 | 0.01 | 0.02 | 0.00 | 0.00 | 0.00 |

TABLE 4-continued

ELISA results for variants of the ZFP "8196" with different center linkers

| Sequence of the center linker | ELISA score for binding to targets having the indicated gap [score is normalized to 8196 bound to its non-gapped target (underlined entry)] 0-bp gap — | 1-bp gap A | 1-bp gap C | 1-bp gap G | 1-bp gap T | average ratio of 1 bp:0 bp score | 2-bp gap TC | 2-bp gap AC | 2-bp gap TG |
|---|---|---|---|---|---|---|---|---|---|
| TGGGGSQKP (SEQ ID NO: 2) | 0.00 | 0.00 | 0.00 | 0.00 | 0.00 | 1.20 | 0.00 | 0.00 | 0.00 |
| LRQKDERP (SEQ ID NO: 3) | 0.01 | 0.01 | 0.01 | 0.04 | 0.08 | 3.49 | 0.00 | 0.00 | 0.00 |
| TGEGGKP (SEQ ID NO: 48) | 0.10 | 0.00 | 0.00 | 0.03 | 0.03 | 0.15 | 0.00 | 0.00 | 0.00 |
| TPDAPKPKP (SEQ ID NO: 49) | 0.02 | 0.16 | 0.13 | 0.68 | 0.95 | 23.75 | 0.01 | 0.00 | 0.01 |
| TPGLHRPKP (SEQ ID NO: 50) | 0.04 | 0.19 | 0.10 | 0.65 | 0.81 | 10.94 | 0.01 | 0.00 | 0.01 |
| TEPRAKPPKP (SEQ ID NO: 51) | 0.01 | 0.39 | 0.17 | 0.78 | 0.93 | 70.72 | 0.02 | 0.01 | 0.01 |
| TPSHTPRPKP (SEQ ID NO: 52) | 0.02 | 0.30 | 0.13 | 0.84 | 0.80 | 25.10 | 0.02 | 0.01 | 0.01 |
| TGYSIPRPKP (SEQ ID NO: 53) | 0.01 | 0.13 | 0.06 | 0.43 | 0.55 | 44.57 | 0.01 | 0.00 | 0.01 |
| TYPRPIAAKP (SEQ ID NO: 54) (designated 1f) | 0.01 | 0.41 | 0.14 | 0.65 | 0.64 | 82.25 | 0.01 | 0.00 | 0.01 |
| THPRAPIPKP (SEQ ID NO: 55) (designated 1c) | 0.00 | 0.20 | 0.09 | 0.57 | 0.60 | 78.86 | 0.01 | 0.00 | 0.00 |
| TPNRRPAPKP (SEQ ID NO: 56) (designated 1d) | 0.00 | 0.23 | 0.09 | 0.52 | 0.52 | 90.27 | 0.01 | 0.01 | 0.01 |
| TSPRLPAPKP (SEQ ID NO: 57) | 0.01 | 0.26 | 0.14 | 0.62 | 0.81 | 67.95 | 0.01 | 0.00 | 0.01 |
| TCPRPPTRKP (SEQ ID NO: 58) | 0.00 | 0.18 | 0.05 | 0.48 | 0.62 | 70.16 | 0.01 | 0.00 | 0.01 |
| TSSPRSNAKP (SEQ ID NO: 59) | 0.01 | 0.05 | 0.02 | 0.20 | 0.25 | 20.85 | 0.01 | 0.00 | 0.01 |
| TVSPAPCRSKP (SEQ ID NO: 60) | 0.01 | 0.03 | 0.01 | 0.14 | 0.19 | 11.52 | 0.02 | 0.00 | 0.01 |
| TPDRPISTCKP (SEQ ID NO: 61) | 0.01 | 0.11 | 0.05 | 0.29 | 0.47 | 15.41 | 0.03 | 0.01 | 0.02 |

TABLE 5

ELISA results for variants of the ZFP "7263" with different center linkers

ELISA score for binding to targets having the indicated gap
[score is normalized to 7263 bound to its non-gapped target
(underlined entry)]

| Sequence of the center linker | 0-bp gap — | 1-bp gap | | | | average ratio of 1 bp:0 bp score | 2-bp gap | | |
|---|---|---|---|---|---|---|---|---|---|
| | | A | C | G | T | | AC | AT | CT |
| TGSQKP (SEQ ID NO: 72) | <u>1.00</u> | 0.01 | 0.01 | 0.03 | 0.02 | 0.02 | 0.01 | 0.01 | 0.00 |
| TGGGGSQKP (SEQ ID NO: 2) | 0.51 | 0.06 | 0.05 | 0.41 | 0.39 | 0.44 | 0.01 | 0.01 | 0.02 |
| LRQKDERP (SEQ ID NO: 3) | 0.25 | 0.03 | 0.02 | 0.18 | 0.13 | 0.36 | 0.01 | 0.01 | 0.01 |
| TGEGGKP (SEQ ID NO: 48) | 1.30 | 0.02 | 0.02 | 0.05 | 0.04 | 0.03 | 0.01 | 0.01 | 0.01 |
| TPRPPIPKP (SEQ ID NO: 4) | 0.14 | 0.97 | 0.67 | 1.85 | 2.09 | 10.20 | 0.02 | 0.01 | 0.01 |
| TQRPQIPPKP (SEQ ID NO: 62) | 0.15 | 1.66 | 1.00 | 2.86 | 3.05 | 14.68 | 0.03 | 0.02 | 0.01 |
| TPNRCPPTKP (SEQ ID NO: 63) | 0.31 | 1.68 | 1.13 | 2.62 | 3.16 | 7.53 | 0.03 | 0.02 | 0.01 |
| TYPRPLLAKP (SEQ ID NO: 7) | 0.29 | 1.95 | 1.27 | 3.88 | 3.97 | 10.08 | 0.03 | 0.01 | 0.01 |
| TPLCQRPMKQKP (SEQ ID NO: 8) | 0.28 | 1.82 | 1.28 | 3.44 | 4.00 | 10.88 | 0.08 | 0.05 | 0.02 |

TABLE 6

ELISA results for variants of the ZFP "7264" with different center linkers

ELISA score for binding to targets having the indicated gap
[score is normalized to 7264 bound to its non-gapped target
(underlined entry)]

| Sequence of the center linker | 0-bp gap — | 1-bp gap | | | | average ratio of 1 bp:0 bp score | 2-bp gap | | |
|---|---|---|---|---|---|---|---|---|---|
| | | A | C | G | T | | TT | TA | CT |
| TGSQKP (SEQ ID NO: 72) | <u>1.00</u> | 0.00 | 0.00 | 0.00 | 0.00 | 0.00 | 0.00 | 0.00 | 0.00 |
| TGGGGSQKP (SEQ ID NO: 2) | 0.46 | 0.07 | 0.04 | 0.08 | 0.17 | 0.19 | 0.03 | 0.03 | 0.07 |
| LRQKDERP (SEQ ID NO: 3) | 0.26 | 0.05 | 0.03 | 0.06 | 0.10 | 0.22 | 0.02 | 0.02 | 0.02 |
| TGEGGKP (SEQ ID NO: 48) | 1.39 | 0.02 | 0.03 | 0.05 | 0.08 | 0.03 | 0.03 | 0.02 | 0.03 |
| TGLPKPKP (SEQ ID NO: 64) | 0.14 | 0.19 | 0.11 | 0.38 | 0.86 | 2.84 | 0.03 | 0.02 | 0.02 |
| TSRPRPKP (SEQ ED NO: 11) | 0.18 | 0.52 | 0.22 | 0.77 | 2.07 | 4.93 | 0.03 | 0.03 | 0.03 |

TABLE 6-continued

ELISA results for variants of the ZFP "7264" with different center linkers

ELISA score for binding to targets having the indicated gap
[score is normalized to 7264 bound to its non-gapped target
(underlined entry)]

| Sequence of the center linker | 0-bp gap — | 1-bp gap | | | | average ratio of 1 bp:0 bp score | 2-bp gap | | |
|---|---|---|---|---|---|---|---|---|---|
| | | A | C | G | T | | TT | TA | CT |
| TLPLPRPKP (SEQ ID NO: 65) | 0.25 | 0.58 | 0.25 | 0.85 | 1.36 | 3.01 | 0.04 | 0.03 | 0.03 |
| TVPRPTPPKP (SEQ ID NO: 12) (designated 1e) | 0.16 | 2.35 | 1.02 | 1.58 | 2.55 | 11.71 | 0.05 | 0.05 | 0.06 |
| TLPPCFRPKP (SEQ ID NO: 66) | 0.36 | 0.72 | 0.25 | 0.77 | 2.72 | 3.11 | 0.06 | 0.06 | 0.05 |
| TKHGTPKHREDKP (SEQ ID NO: 13) | 0.01 | 0.01 | 0.01 | 0.01 | 0.01 | 0.79 | 0.00 | 0.00 | 0.00 |

To further support and expand upon the results obtained in the ELISA studies, ZFPs with selected linkers were evaluated for in vivo cleavage activity at various target sites using the yeast screening assay described in International Patent Publication WO 2009/042163. As these experiments are more labor intensive, they were performed on fewer ZFPs. For these studies, six ZFPs from Table 5 and five ZFPs from Table 6 were assembled into constructs that enabled expression as zinc finger nucleases (ZFNs) as described in WO 2007/139982. In vivo activity was then measured by evaluating MEL-1 secretion from yeast strains having various target sites. The target sequences used for these studies are provided in Tables 7 and 8, and included variations of the 7263 and 7264 binding sites with central insertions of 0, 1-, or 2-bp.

TABLE 7

Targets used for yeast screening assay of ZFPs selected to skip a 1 bp gap in ZFP7263

| ZFP w/randomized Gap linker | Sequence | Target sites |
|---|---|---|
| 7263 | — | ACTCTGTGGAAG (SEQ ID NO: 95) |
| | A | ACTCTGaTGGAAG (SEQ ID NO: 96) |
| | C | ACTCTGcTGGAAG (SEQ ID NO: 97) |
| | G | ACTCTGgTGGAAG (SEQ ID NO: 98) |
| | T | ACTCTGtTGGAAG (SEQ ID NO: 99) |
| | AC | ACTCTGacTGGAAG (SEQ ID NO: 100) |
| | AT | ACTCTGatTGGAAG (SEQ ID NO: 101) |

TABLE 7-continued

Targets used for yeast screening assay of ZFPs selected to skip a 1 bp gap in ZFP7263

| ZFP w/randomized Gap linker | Sequence | Target sites |
|---|---|---|
| | CT | ACTCTGctTGGAAG (SEQ ID NO: 102) |

Reporter plasmids bearing nuclease target sites were constructed essentially as described in International Patent Publication WO 2009/042163, except that nuclease target cassettes had the general form of GATCTGTTGGAGCCGCTTTAACCC(X)$_{12-14}$TGCTCGCG (SEQ ID NO:103) where (1) the four underlined bases at either end represent the overhangs used for cloning into the BamHI/BssHII digested reporter plasmid, (2) the italicized sequence represents the binding site for the 7264 ZFN which binds to the antisense strand and was invariant for these screens, and (3) (X)$_{12-14}$ was replaced with sequences listed in the table. Capitalized bases indicate the binding sequences for the four fingers of each host ZFP, while lowercase letters indicate inserted nucleotides (or "gap" bases).

TABLE 8

Targets used for yeast screening assay of ZFPs selected to skip a 1 bp gap in ZFP7264

| ZFP w/randomized Gap linker | Sequence | Target sites |
|---|---|---|
| 7264 | — | AAAGCGGCTCCG (SEQ ID NO: 104) |
| | A | AAAGCGaGCTCCG (SEQ ID NO: 105) |
| | C | AAAGCGcGCTCCG (SEQ ID NO: 106) |

TABLE 8-continued

Targets used for yeast screening assay of
ZFPs selected to skip a 1 bp gap in ZFP7264

| ZFP w/randomized linker | Gap Sequence | Target sites |
|---|---|---|
| | G | AAAGCGgGCTCCG (SEQ ID NO: 107) |
| | T | AAAGCGtGCTCCG (SEQ ID NO: 108) |
| | TT | AAAGCGttGCTCCG (SEQ ID NO: 109) |
| | TA | AAAGCGtaGCTCCG (SEQ ID NO: 110) |
| | CT | AAAGCGctGCTCCG (SEQ ID NO: 111) |

Reporter plasmids bearing nuclease target sites were constructed essentially as described in International Patent Publication WO 2009/042163, except that nuclease target cassettes had the general form of GATCTGTT(X)$_{12-14}$AACCCACTCTGTGGAAGTGCT CGCG (SEQ ID NO:112) where (1) the four underlined bases at either end represent the overhangs used for cloning into the BamHI/BssHII digested reporter plasmid, (2) the italicized sequence represents the binding site for the 7263 ZFN which was invariant for these screens, and (3) (X)$_{12-14}$ was replaced with sequences listed in the table. Capitalized bases indicate the binding sequences for the four fingers of each host ZFP, while lowercase letters indicate inserted nucleotides (or "gap" bases). Note that the target sites listed in the table are the reverse complement of what is present in the target cassette as the 7264 ZFN binds to the antisense strand.

Data for these experiments are shown in Tables 9 and 10, with each table listing data for proteins derived from a different host ZFN. Table 9 provides data for 7263-derived ZFNs and Table 10 provides data for 7264-derived ZFNs. In each table, nuclease activity data for the host ZFN is listed in the top row, followed by nuclease activity data for one control protein in row 2, followed by data for the ZFPs selected from the phage display libraries. Since ZFP7263 and ZFP7264 are two halves of the same zinc-finger nuclease dimer, the data for the host ZFN is the same in each table. The results of these studies broadly matched the patterns observed in the ELISA studies, in that the ZFNs bearing phage-selected linkers showed both higher activity and better preference for targets bearing a 1 bp insert than ZFPs bearing control linkers.

TABLE 9

Yeast screening results for variants of ZFP7263 with different center linkers

MEL-1 score for nuclease activity at targets having the indicated gap [score is normalized to ZFP7263 bound to its non-gapped target (underlined entry)]

| Sequence of the center linker | 0-bp gap | 1-bp gap | | | | average ratio of 1 bp:0 bp score | 2-bp gap | | |
|---|---|---|---|---|---|---|---|---|---|
| | — | A | C | G | T | | AC | AT | CT |
| TGSQKP (SEQ ID NO: 72) | 1.00 | 0.05 | 0.05 | 0.09 | 0.06 | 0.06 | 0.09 | 0.02 | 0.08 |
| TGGGGSQKP (SEQ ID NO: 2) | 0.11 | 0.14 | 0.04 | 0.60 | 0.31 | 2.57 | 0.04 | 0.02 | 0.04 |
| TPRPPIPKP (SEQ ID NO: 4) | 0.04 | 1.30 | 1.41 | 2.18 | 1.40 | 35.90 | 0.05 | 0.03 | 0.04 |
| TQRPQIPPKP (SEQ ID NO: 62) | 0.04 | 1.05 | 0.43 | 2.18 | 1.19 | 34.18 | 0.03 | 0.02 | 0.03 |
| TPNRCPPTKP (SEQ ID NO: 63) | 0.05 | 1.30 | 0.34 | 2.85 | 1.59 | 33.22 | 0.04 | 0.03 | 0.06 |
| TYPRPLLAKP (SEQ ID NO: 7) | 0.05 | 0.69 | 0.37 | 2.21 | 1.06 | 20.15 | 0.10 | 0.05 | 0.05 |
| TPLCQRPMKQKP (SEQ ID NO: 8) | 0.04 | 0.97 | 0.30 | 1.52 | 1.19 | 27.52 | 1.05 | 0.01 | 0.03 |

TABLE 10

Yeast screening results for variants of the ZFP7264 with different center linkers MEL-1 score for nuclease activity at targets having the indicated gap [score is normalized to ZFP7264 bound to its non-gapped target (underlined entry)]

| Sequence of the center linker | 0-bp gap | 1-bp gap | | | | average ratio of 1 bp:0 bp score | 2-bp gap | | |
|---|---|---|---|---|---|---|---|---|---|
| | – | A | C | G | T | | TT | TA | CT |
| TGSQKP (SEQ ID NO: 72) | 1.00 | 0.05 | 0.05 | 0.09 | 0.06 | 0.06 | 0.09 | 0.02 | 0.08 |
| TGGGGSQKP (SEQ ID NO: 2) | 0.28 | 0.08 | 0.07 | 0.14 | 0.34 | 0.57 | 0.12 | 0.09 | 0.15 |
| TGLPKPKP (SEQ ID NO: 64) | 0.04 | 0.08 | 0.07 | 0.42 | 0.79 | 8.03 | 0.11 | 0.08 | 0.09 |
| TSRPRPKP (SEQ ID NO: 11) | 0.08 | 0.18 | 0.08 | 0.61 | 3.38 | 13.33 | 0.03 | 0.07 | 0.10 |
| TVPRPTPPKP (SEQ ID NO: 12) (designated 1e) | 0.08 | 1.24 | 0.14 | 1.40 | 2.34 | 20.28 | 0.12 | 0.09 | 0.11 |

Figure 5:
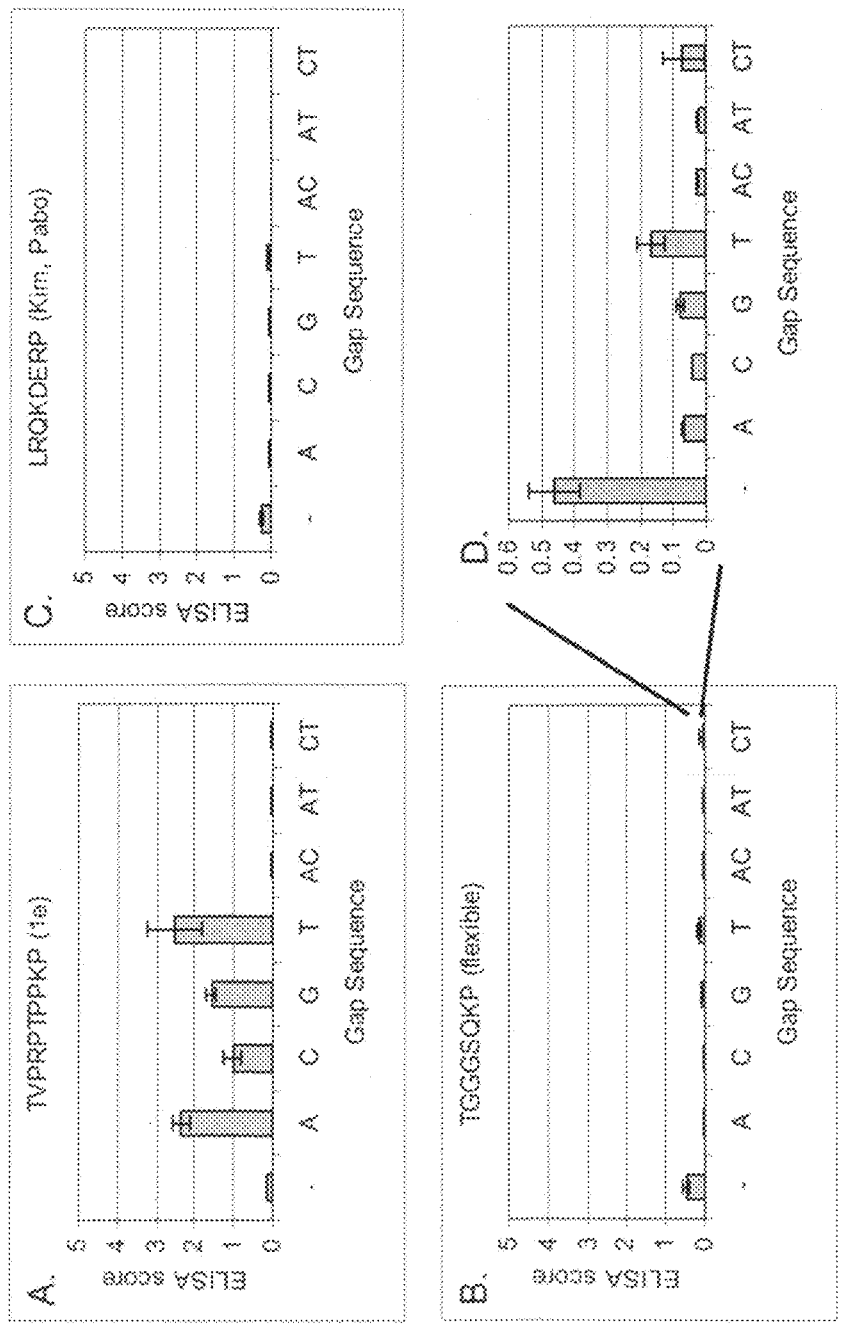
FIG. 5, panels A through D, are graphs depicting gap selectivity for linkers selected to skip 1 base pair in ZFP7264.

Since the ELISA was in close concordance with the yeast screening data, we chose a set of exemplary 1 bp-skipping linkers that performed among the best in the ELISA assay. These are listed in Table 11 and are designated "1c", "1d", "1e", and "1f". These designations are also included in the data presented in Tables 4, 6, and 10. The ELISA data for these exemplary linkers is also shown in FIGS. 4 and 5.

TABLE 11

Exemplary linker designs

| Linker Sequence | Linker Designation | Number of Bases Skipped |
|---|---|---|
| THPRAPIPKP (SEQ ID NO: 55) | 1c | 1 |
| TPNRRPAPKP (SEQ ID NO: 56) | 1d | 1 |
| TVPRPTPPKP (SEQ ID NO: 12) | 1e | 1 |
| TYPRPIAAKP (SEQ ID NO: 54) | 1f | 1 |

As stated previously in Example 1, target sites used for selection (Table 2a) contained degenerate bases in the gap in order to favor the selection of linkers that exhibited no inherent preference for particular gap sequences. The data shown in FIGS. 4 and 5 suggest that this selection strategy was successful: proteins bearing the exemplary linkers exhibit little variation in binding among targets with gap bases of A, G, C or T. Moreover, the minor amount of variation that is observed is mirrored in the results obtained with control flexible liners (see, e.g., FIG. 5D for flexible linker (TGGGGSQKP) (SEQ ID NO:2)) indicating that variation is a property of the flanking fingers.

An analogous ELISA experiment was performed for linkers selected to skip a 2 basepair gap in the context of ZFP8196. Two additional control proteins were generated by replacing the central linker of each host ZFP with two alternative, previously characterized, linker sequences which collectively represented the state of the art for spanning 2 bp. The sequences of these control linkers were TGGGGSGGGSQKP (SEQ ID NO:14) and LRQKDGGGSERP (SEQ ID NO:68). These control proteins, as well as the host ZFPs, were also included in the ELISA studies. ZFPs were tested for binding to target sites containing either no gap, each of the 4 possible 1 basepair gaps, and each of the 16 possible 2 basepair gaps. Target sites are listed in Table 12. ELISA scores were normalized to the score of the 8196 ZFP bound to its non-gapped target site. Exemplary linkers were chosen based on their ELISA behavior in a similar fashion to the 1 bp-skipping linkers. These exemplary linkers were designated "2d", "2e", and "2f". The ELISA results for the exemplary linkers in the 8196 ZFP and control ZFPs are shown in FIG. 6. As seen in FIG. 6, neither of the ZFPs bearing the control linkers shows a preference for a target site with a 2 basepair gap. However, the ZFPs with the selected linkers showed clear preferences for a 2 basepair gap over both the 1 basepair and non-gapped target sites.

TABLE 12

Target sites used for ELISA characterization of 2 bp-skipping linkers

| ZFP w/randomized linker | Gap Sequence | Target sites |
|---|---|---|
| 8196 | – | ATAAACTGCAAAAGGC (SEQ ID NO: 32) |
| | A | ATAAACTGaCAAAAGGC (SEQ ID NO: 73) |
| | C | ATAAACTGcCAAAAGGC (SEQ ID NO: 74) |

TABLE 12-continued

Target sites used for ELISA characterization of 2 bp-skipping linkers

| ZFP w/randomized linker | Gap Sequence | Target sites |
|---|---|---|
| | G | AT<u>AAACTG</u>g<u>CAAAAGGC</u> (SEQ ID NO: 75) |
| | T | AT<u>AAACTG</u>t<u>CAAAAGGC</u> (SEQ ID NO: 76) |
| | AA | AT<u>AAACTG</u>aa<u>CAAAAGGC</u> (SEQ ID NO: 113) |
| | AC | AT<u>AAACTG</u>ac<u>CAAAAGGC</u> (SEQ ID NO: 114) |
| | AG | AT<u>AAACTG</u>ag<u>CAAAAGGC</u> (SEQ ID NO: 115) |
| | AT | AT<u>AAACTG</u>at<u>CAAAAGGC</u> (SEQ ID NO: 116) |
| | CA | AT<u>AAACTG</u>ca<u>CAAAAGGC</u> (SEQ ID NO: 117) |
| | CC | AT<u>AAACTG</u>cc<u>CAAAAGGC</u> (SEQ ID NO: 118) |
| | CG | AT<u>AAACTG</u>cg<u>CAAAAGGC</u> (SEQ ID NO: 119) |
| | CT | AT<u>AAACTG</u>ct<u>CAAAAGGC</u> (SEQ ID NO: 120) |
| | GA | AT<u>AAACTG</u>ga<u>CAAAAGGC</u> (SEQ ID NO: 121) |
| | GC | AT<u>AAACTG</u>gc<u>CAAAAGGC</u> (SEQ ID NO: 122) |
| | GG | AT<u>AAACTG</u>gg<u>CAAAAGGC</u> (SEQ ID NO: 123) |
| | GT | AT<u>AAACTG</u>gt<u>CAAAAGGC</u> (SEQ ID NO: 124) |
| | TA | AT<u>AAACTG</u>ta<u>CAAAAGGC</u> (SEQ ID NO: 125) |
| | TC | AT<u>AAACTG</u>tc<u>CAAAAGGC</u> (SEQ ID NO: 126) |
| | TG | AT<u>AAACTG</u>tg<u>CAAAAGGC</u> (SEQ ID NO: 127) |
| | TT | AT<u>AAACTG</u>tt<u>CAAAAGGC</u> (SEQ ID NO: 128) |

Table 12: Duplex DNA target sites used in ELISA characterization studies had the general form of: TTAG(X)$_{16-18}$TATC, (SEQ ID NO: 6) where (X)$_{16-18}$ was replaced with sequences listed in the table.
DNA duplexes were made by annealing complementary oligonucleotides. Oligonucleotides complementary to the sequences listed in the table contained a 5' biotin.
Underlined bases indicate the binding sequences for the four fingers of each host ZFP, while lowercase bases indicate inserted nucleotides (or "gap" bases).

As stated previously in Example 1, target sites used for selection (Table 2a) contained degenerate bases in the gap in order to favor the selection of linkers that exhibited no inherent preference for particular gap sequences. Shown in FIG. 6 is an expansion of the scale for one of the flexible linkers (TGGGGSGGGSQKP (SEQ ID NO:14)). This flexible linker should not have any interaction with the target site, and thus the pattern seen is likely due to the binding of the zinc finger proteins. The fact that the exemplary linkers show a similar pattern of binding to 2 basepair gap target sites suggests that the selected linkers also should not impose any gap compositional bias in ZFP binding.

A more concise summary of this data is presented in Table 13, where ELISA scores were averaged over all of the 1 or 2 basepair gap compositions. Also reported is the fold preference for a 2 basepair gap over the 1 basepair gap and the non-gapped target. The most selective linker (TPNPHRRTDPSHKP (SEQ ID NO:69), "2f") represents an improvement in 2 basepair gap selectivity of >100-fold over a zero basepair gap and >20-fold over a 1 basepair gap compared to the control linkers.

TABLE 13

Summary of ELISA data for 2-bp skipping linkers

| Linker Sequence | Designation | Average Normalized ELISA Score (gap) | | | 2 bp-Gap Selectivity vs: | |
|---|---|---|---|---|---|---|
| | | 0 bp | 1 bp | 2 bp | 0 bp | 1 bp |
| TGGGGSGGGSQKP (SEQ ID NO: 14) | flexible | 0.019 | 0.041 | 0.010 | 0.6 | 0.2 |
| LRQKDGGGSERP (SEQ ID NO: 68) | Kim, Pabo | 0.010 | 0.047 | 0.003 | 0.4 | 0.1 |
| TPNPHRRTDPSHKP (SEQ ID NO: 69) | 2f | 0.003 | 0.046 | 0.219 | 64.6 | 4.7 |
| TLAPRPYRPPKP (SEQ ID NO: 70) | 2d | 0.005 | 0.035 | 0.127 | 24.4 | 3.6 |
| TPGGKSSRTDRNKP (SEQ ID NO: 71) | 2e | 0.005 | 0.099 | 0.100 | 22.0 | 1.0 |

Example 3

ELISA Characterization of Linkers in Various Host ZFPs

To demonstrate the generality of the exemplary linkers, the four 1 bp-skipping linkers listed in Table 11 (1c-1f) were cloned into twelve different host ZFPs. The host ZFPs were designated ZFP1, ZFP2 etc. The resultant proteins were expressed via in vitro transcription and translation and tested via ELISA, as described above. For comparison, we also tested the host ZFPs with a flexible linker (TGGGGSQKP (SEQ ID NO:2)), and the results are presented in FIG. 7. This data demonstrates that relative to a standard flexible linker, the new linkers significantly increased the ELISA score of most host ZFPs, with the only exceptions being ZFPs that either saturate the assay (ZFP1 and ZFP2) or for which binding is undetectably low (ZFP 11 and ZFP 12). Average fold increases in ELISA score across all host ZFPs were from 3-5.

In a similar study, the three exemplary linkers selected to skip a 2 bp gap listed in Table 13 (2d-2f) were tested in six different host ZFPs as described above (ZFP13, ZFP14, etc.), and these results are presented in FIG. 8. In these experiments, average fold improvements in ELISA score across all host ZFPs ranged from 1.9 to 2.4.

Example 4

Characterization of ZFNs with Exemplary Linkers at Endogenous Loci in Mammalian Cells ZFNs were then tested for their ability to induce double-stranded breaks at endogenous loci. Briefly, a plasmid encoding the 18 ZFNs (ZFP-FokI fusions) described above (Example 3) were paired with their appropriate partner ZFNs and introduced into K562 cells by transfection using the Amaxa™ Nucleofection kit as specified by the manufacturer. To determine the ZFN activity at the target locus as measured by the level of non-homologous end joining (NHEJ), CEL-I mismatch assays were performed essentially as per the manufacturer's instructions (Transgenomic SURVEYOR™). Cells were harvested and chromosomal DNA prepared using a Quickextract™ Kit according to manufacturer's directions (Epicentre®). The appropriate region of the target locus was PCR amplified using Accuprime™ Taq High-fidelity DNA polymerase (Invitrogen) followed by treatment with the CEL-I enzyme.

Figure 9:
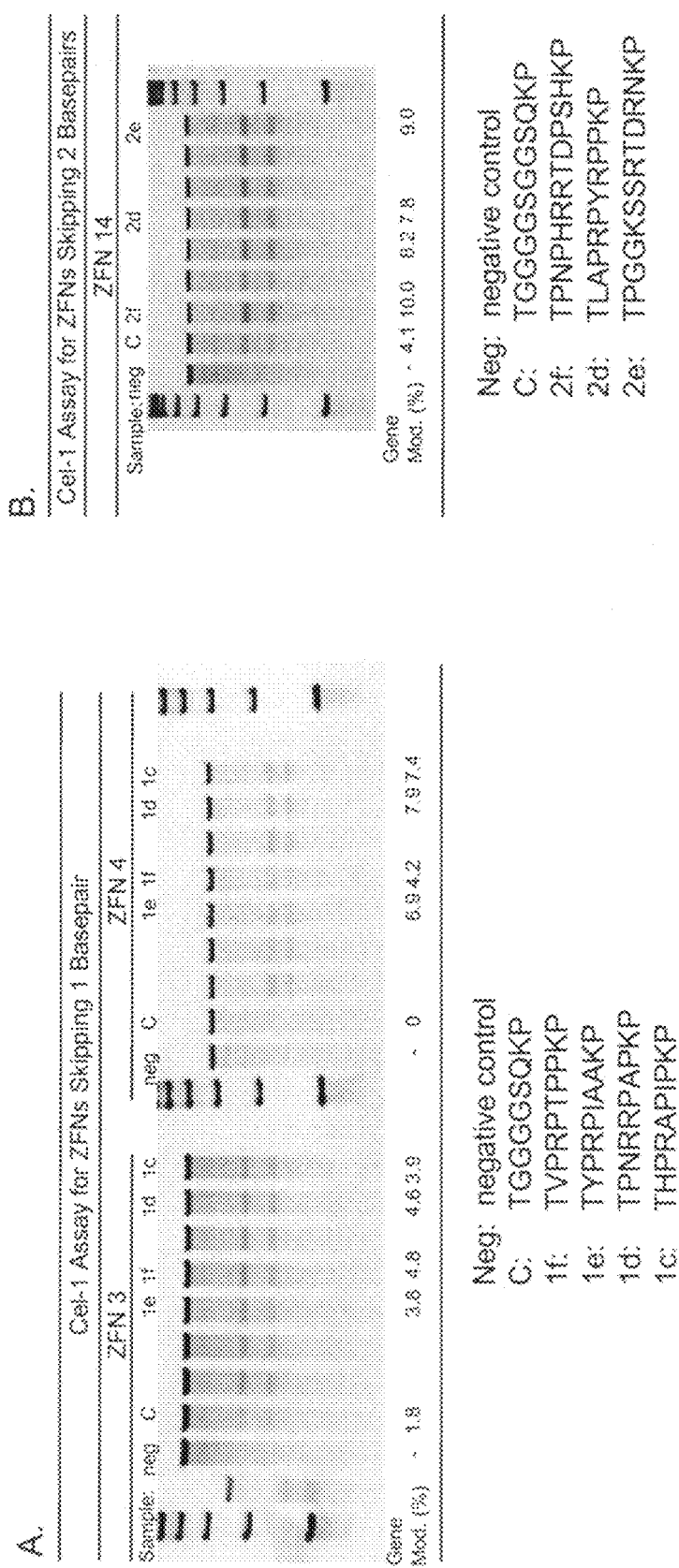
FIG. 9, panels A and B, depict results of endogenous gene modification studies, as determined by CEL-I assays, with ZFNs containing selected linkers.

Example gels generated for the CEL-1 assay are shown in FIG. 9. FIG. 9A shows screening data for ZFN3 and ZFN4 (ZFNs skipping 1 basepair) as the host ZFN whereas FIG. 9B shows the screening data for ZFN14 (ZFN skipping 2 basepairs) as the host ZFN. The data for all the 1 bp skipping exemplary linkers is summarized in FIG. 10 (ZFN1-ZFN12). Some of the ZFNs were expressed using a high expression condition. The high expression is obtained post-transfection by incubating cells at 37° C. for 24 hours and then incubating at 30° C. for 48 hours before genomic DNA was isolated. The ZFNs utilizing this condition are highlighted in FIG. 10. Notably, three ZFNs that were inactive with the TGGGGSQKP (SEQ ID NO:2) linker ("flexible linker") (ZFNs 4, 9 and 10) become active when using a linker as described herein. For these cases, a value of 1.0% modification was assigned to the flexible linker for normalization purposes (the detection limit of the assay). In 85% of the ZFNs tested with the new linkers, an increase in the level of gene modification was observed, with an average increase in approximately 1.8-2.8 fold across the nine active ZFN pairs.

Similarly, the ZFNs described above (Example 3) containing the 2 bp skipping exemplary linkers (ZFN13-ZFN18) were tested at endogenous loci and the results are summarized in FIG. 11. In this study, substitution of the linkers described herein improved activity as compared to the flexible linker for 3 out of 4 active ZFNs, and the average improvement was 1.5-2 fold across all active ZFN pairs.

Example 5

Secondary Selections for a 2-bp Skipping Linker

Figure 12:
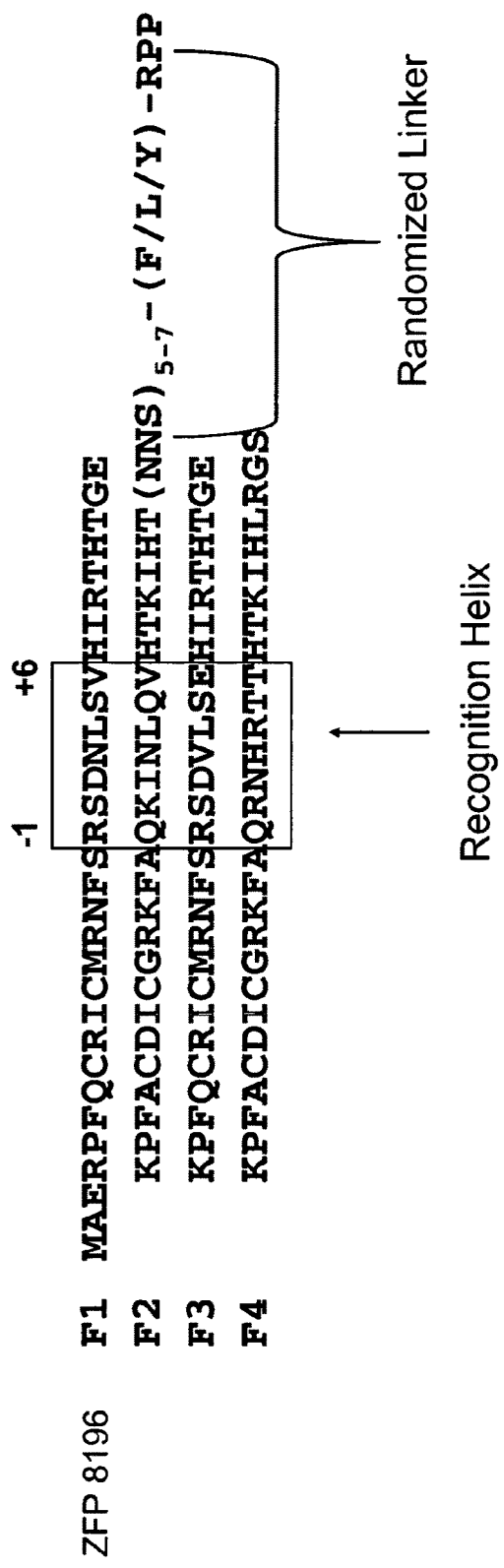
FIG. 12, shows the amino acid sequence of the host ZFP8196 used for the secondary selection for linkers spanning a 2-bp gap. Amino acids are designated by single letter code. The sequence is listed in the amino terminal a carboxy terminal direction, so that the amino terminus of the protein is the first methionine of finger 1, and the carboxy terminus is the final serine of finger 4. "F1" (SEQ ID NO:130), "F2" (SEQ ID NO:131 213), "F3" (SEQ ID NO:132) and "F4" (SEQ ID NO:133) designate the first, second, third and fourth fingers, respectively, of the protein. Recognition helices are boxed. The linker library was generated by replacing codons for two residues in the central linker with a mixture of five to seven fully randomized codons, followed by one codon randomized to obtain either phenylalanine (F), lysine (L), or tyrosine (Y) residues, and the final three codons were fixed to be arginine (R), proline (P), and proline (P). Library codons are denoted by (NNS)5-7 and (F/L/Y).

A secondary set of libraries were constructed based on information obtained from the initial selections for a 2-bp skipping linker (Example 3 and FIG. 3). These libraries fixed the three carboxy-terminal residues of the linker as RPP (lysine, proline, proline) and randomized the remaining amino-terminal residues. The library design is shown in FIG. 12.

Selections were performed in the same manner as in Example 1 using ZFP8196 as the host protein. Gap selectivity of the selected phage pool is shown in FIG. 13A, and the sequences of the linkers from individual clones are shown in FIG. 13B.

An ELISA experiment was performed on each of the individual clones from the secondary selection (FIG. 13B), similar to that of Example 2. ZFPs were tested for binding to target sites containing either no gap, a pool of the 4 possible 1 basepair gaps, and a pool of the 16 possible 2 basepair gaps. Target sites are listed in Table 12. ELISA scores were normalized to the score of the host ZFP8196 bound to its non-gapped target site. The ELISA results for ZFPs bearing linkers that showed both a good normalized ELISA score on the pool of 2-bp gap target sites and good gap selectivity are shown in Table 14.

TABLE 14

Summary of ELISA data for 2-bp skipping linkers

| Linker Sequence | Average Normalized ELISA Score (gap) | | | 2 bp-Gap Selectivity vs: | |
|---|---|---|---|---|---|
| | 0 bp | 1 bp | 2 bp | 0 bp | 1 bp |
| TETTRPFRPPKP (Residues 6-17 of SEQ ID NO: 183) | 0.001 | 0.001 | 0.570 | 570.0 | 570.0 |
| TGSLRPYRRPKP (SEQ ID NO: 9) | 0.001 | 0.010 | 0.310 | 310.0 | 31.0 |

TABLE 14-continued

Summary of ELISA data for 2-bp skipping linkers

| Linker Sequence | Average Normalized ELISA Score (gap) | | | 2 bp-Gap Selectivity vs: | |
|---|---|---|---|---|---|
| | 0 bp | 1 bp | 2 bp | 0 bp | 1 bp |
| TSINRPFRRPKP (SEQ ID NO: 10) | 0.010 | 0.020 | 0.570 | 57.0 | 28.5 |
| TNTTRPYRPPKP (Residues 6-17 of SEQ ID NO: 175) | 0.001 | 0.010 | 0.410 | 410.0 | 41.0 |
| TASCPRPFRPPKP (Residues 6-18 of SEQ ID NO: 194) | 0.010 | 0.020 | 0.370 | 37.0 | 18.5 |
| TGEARPYRPPKP (Residues 6-18 of SEQ ID NO: 178) | 0.001 | 0.010 | 0.610 | 610.0 | 61.0 |

As shown, ZFPs with the selected linkers showed clear preferences for a 2 basepair gap over both the 1 basepair and non-gapped target sites.

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. A zinc finger protein comprising a plurality of non-naturally occurring zinc finger modules, wherein at least two of the non-naturally occurring zinc finger DNA-binding modules are joined by an amino acid linker sequence of 5 to 20 amino acid residues between the last residue of the N-terminal zinc finger module and the first residue of C-terminal zinc finger module, the amino acid linker comprising an N-terminal amino acid residue adjacent to the N-terminal zinc finger module, a C-terminal amino acid residue adjacent to the C-terminal zinc finger module, and amino acid residues internal to the N- and C-terminal amino acid linker residues, wherein
   (i) the N-terminal amino acid linker residue or the internal amino acid linker residues comprises at least one proline residue;
   (ii) the zinc finger protein binds to a target site comprising target subsites bound by each zinc finger module; and
   (iii) there is a gap of 0, 1, 2 or 3 base pairs between the target subsites bound by the zinc finger DNA-binding modules joined by the amino acid linker.

2. The zinc finger protein of claim 1, wherein the linker further comprises at least two basic amino acid residues.

3. The zinc finger protein of claim 2, wherein the basic amino acid residues are selected from the group consisting of an arginine residue, a histidine residue, a lysine residue or combinations thereof.

4. The zinc finger protein of claim 1, wherein one or more of the zinc finger proteins further comprises a regulatory domain.

5. The zinc finger protein of claim 4, wherein the regulatory domain is a transcriptional modulating domain.

6. The zinc finger protein of claim 5, wherein the regulatory domain is an activation domain or a repression domain.

7. The zinc finger protein of claim 4, wherein the regulatory domain is a cleavage domain or cleavage half-domain.

8. An isolated polynucleotide encoding the zinc finger protein according to claim 1.

9. An isolated cell comprising the zinc finger protein according to claim 1.

10. An isolated cell comprising the polynucleotide according to claim 8.

11. A method of modulating expression of a gene in a cell, the method comprising administering the zinc finger protein according to claim 1.

12. The method of claim 11, wherein the zinc finger protein is administered to the cell as a polynucleotide.

13. The method of claim 11, wherein the modulation comprises up or down regulation of the gene.

14. The method of claim 11, wherein the modulation comprises cleavage of the gene.

15. The method of claim 11, wherein the gene is an endogenous cellular gene.

* * * * *

SEQUENCE LISTING

```
<160> NUMBER OF SEQ ID NOS: 213

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Thr Gly Glu Lys Pro
1               5

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Thr Gly Gly Gly Gly Ser Gln Lys Pro
1               5

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3
```

Leu Arg Gln Lys Asp Glu Arg Pro
1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Thr Pro Arg Pro Pro Ile Pro Lys Pro
1               5

<210> SEQ ID NO 5
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (7)..(26)
<223> OTHER INFORMATION: This region may encompass any of SEQ ID NOS
      32-46

<400> SEQUENCE: 5
tataatnnnn nnnnnnnnnn nnnnnnttca cagtcagtcc acacgtc                47

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (5)..(22)
<223> OTHER INFORMATION: This region may encompass any of SEQ ID NOS 32,
      73-76, or 113-128

<400> SEQUENCE: 6 ttagnnnnn nnnnnnnnnn nntatc                                        26

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Thr Tyr Pro Arg Pro Leu Leu Ala Lys Pro
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Thr Pro Leu Cys Gln Arg Pro Met Lys Gln Lys Pro

```
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Thr Gly Ser Leu Arg Pro Tyr Arg Arg Pro Lys Pro
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Thr Ser Ile Asn Arg Pro Phe Arg Arg Pro Lys Pro
1               5                   10

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Thr Ser Arg Pro Arg Pro Lys Pro
1               5

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Thr Val Pro Arg Pro Thr Pro Pro Lys Pro
1               5                   10

<210> SEQ ID NO 13
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Thr Lys His Gly Thr Pro Lys His Arg Glu Asp Lys Pro
1               5                   10

<210> SEQ ID NO 14
<211> LENGTH: 13
<212> TYPE: PRT
<213> ORGANISM: Artificial Sequence
<220> FEATURE:
<223> OTHER INFORMATION: Description of Artificial Sequence: Synthetic
```

-continued peptide

<400> SEQUENCE: 14

Thr Gly Gly Gly Gly Ser Gly Gly Gly Ser Gln Lys Pro
1               5                   10

<210> SEQ ID NO 15
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Thr Gly Gly Gly Gly Ser Gly Gly Ser Gly Gly Ser Gln Lys Pro
1               5                   10                  15

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Thr Gly Gly Glu Lys Pro
1               5

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Thr Gly Gly Gln Lys Pro
1               5

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Thr Gly Gly Ser Gly Glu Lys Pro
1               5

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Thr Gly Gly Ser Gly Gln Lys Pro
1               5

<210> SEQ ID NO 20

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Thr Gly Gly Ser Gly Gly Ser Gly Glu Lys Pro
1               5                   10

<210> SEQ ID NO 21
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Thr Gly Gly Ser Gly Gly Ser Gly Gln Lys Pro
1               5                   10

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Arg Ser Asp Asn Leu Ser Val
1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gln Lys Ile Asn Leu Gln Val
1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Arg Ser Asp Val Leu Ser Glu
1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25
```

```
Gln Arg Asn His Arg Thr Thr
1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Arg Ser Asp Thr Leu Ser Glu
1               5

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ala Arg Ser Thr Arg Thr Thr
1               5

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Arg Ser Asp Ser Leu Ser Lys
1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gln Arg Ser Asn Leu Lys Val
1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Arg Asn Ala His Arg Ile Asn
1               5

<210> SEQ ID NO 31
<211> LENGTH: 7
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 31

Ala Arg Ser Thr Arg Thr Asn
1               5

<210> SEQ ID NO 32
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
ataaactgca aaaggc                                                    16

<210> SEQ ID NO 33
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
ataaactgdc aaaaggc                                                   17

<210> SEQ ID NO 34
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
ataaactgdb caaaaggc                                                  18

<210> SEQ ID NO 35
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
ataaactgdb bcaaaaggc                                                 19

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
ataaactgdb bbcaaaaggc                                                20

<210> SEQ ID NO 37
<211> LENGTH: 16
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 37
ttaaagcggc tccgaa                                                        16

<210> SEQ ID NO 38
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
ttaaagcghg ctccgaa                                                       17

<210> SEQ ID NO 39
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
ttaaagcghd gctccgaa                                                      18

<210> SEQ ID NO 40
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
ttaaagcghd vgctccgaa                                                     19

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
ttaaagcghd vdgctccgaa                                                    20

<210> SEQ ID NO 42
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
ccactctgtg gaagtg                                                        16

<210> SEQ ID NO 43
<211> LENGTH: 17
<212> TYPE: DNA
<213> ORGANISM: Artificial Sequence
<220> FEATURE:
<223> OTHER INFORMATION: Description of Artificial Sequence: Synthetic

```
                         oligonucleotide

<400> SEQUENCE: 43
ccactctght ggaagtg                                                     17

<210> SEQ ID NO 44
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
ccactctghh tggaagtg                                                    18

<210> SEQ ID NO 45
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
ccactctghh htggaagtg                                                   19

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
ccactctghh hbtggaagtg                                                  20

<210> SEQ ID NO 47
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (27)..(38)
<223> OTHER INFORMATION: Any amino acid and this region may encompass
      2-12 residues

<400> SEQUENCE: 47

Lys Pro Phe Ala Cys Asp Ile Cys Gly Arg Lys Phe Ala Gln Lys Ile
1               5                   10                  15

Asn Leu Gln Val His Thr Lys Ile His Thr Xaa Xaa Xaa Xaa Xaa Xaa
            20                  25                  30

Xaa Xaa Xaa Xaa Xaa Xaa
        35

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 48

Thr Gly Glu Gly Gly Lys Pro
1               5

<210> SEQ ID NO 49
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Thr Pro Asp Ala Pro Lys Pro Lys Pro
1               5

<210> SEQ ID NO 50
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Thr Pro Gly Leu His Arg Pro Lys Pro
1               5

<210> SEQ ID NO 51
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Thr Glu Pro Arg Ala Lys Pro Pro Lys Pro
1               5                   10

<210> SEQ ID NO 52
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Thr Pro Ser His Thr Pro Arg Pro Lys Pro
1               5                   10

<210> SEQ ID NO 53
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Thr Gly Tyr Ser Ile Pro Arg Pro Lys Pro
1               5                   10

<210> SEQ ID NO 54
<211> LENGTH: 10
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 54

Thr Tyr Pro Arg Pro Ile Ala Ala Lys Pro
1               5                   10

<210> SEQ ID NO 55
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Thr His Pro Arg Ala Pro Ile Pro Lys Pro
1               5                   10

<210> SEQ ID NO 56
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Thr Pro Asn Arg Arg Pro Ala Pro Lys Pro
1               5                   10

<210> SEQ ID NO 57
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Thr Ser Pro Arg Leu Pro Ala Pro Lys Pro
1               5                   10

<210> SEQ ID NO 58
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Thr Cys Pro Arg Pro Pro Thr Arg Lys Pro
1               5                   10

<210> SEQ ID NO 59
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Thr Ser Ser Pro Arg Ser Asn Ala Lys Pro
1               5                   10

<210> SEQ ID NO 60
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Thr Val Ser Pro Ala Pro Cys Arg Ser Lys Pro
1               5                   10

<210> SEQ ID NO 61
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Thr Pro Asp Arg Pro Ile Ser Thr Cys Lys Pro
1               5                   10

<210> SEQ ID NO 62
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Thr Gln Arg Pro Gln Ile Pro Pro Lys Pro
1               5                   10

<210> SEQ ID NO 63
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Thr Pro Asn Arg Cys Pro Pro Thr Lys Pro
1               5                   10

<210> SEQ ID NO 64
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Thr Gly Leu Pro Lys Pro Lys Pro
1               5

<210> SEQ ID NO 65
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Thr Leu Pro Leu Pro Arg Pro Lys Pro
1               5

<210> SEQ ID NO 66
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Thr Leu Pro Pro Cys Phe Arg Pro Lys Pro
1               5                   10

<210> SEQ ID NO 67
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (7)..(24)
<223> OTHER INFORMATION: This region may encompass any of SEQ ID NOS 33,
      34, 38, 39, 43, or 44

<400> SEQUENCE: 67
tataatnnnn nnnnnnnnnn nnnnttcaca gtcagtccac acgtc                45

<210> SEQ ID NO 68
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Leu Arg Gln Lys Asp Gly Gly Gly Ser Glu Arg Pro
1               5                   10

<210> SEQ ID NO 69
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Thr Pro Asn Pro His Arg Arg Thr Asp Pro Ser His Lys Pro
1               5                   10

<210> SEQ ID NO 70
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Thr Leu Ala Pro Arg Pro Tyr Arg Pro Pro Lys Pro
1               5                   10

```
<210> SEQ ID NO 71
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Thr Pro Gly Gly Lys Ser Ser Arg Thr Asp Arg Asn Lys Pro
1               5                   10

<210> SEQ ID NO 72
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Thr Gly Ser Gln Lys Pro
1               5

<210> SEQ ID NO 73
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
ataaactgac aaaaggc                                                        17

<210> SEQ ID NO 74
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
ataaactgcc aaaaggc                                                        17

<210> SEQ ID NO 75
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
ataaactggc aaaaggc                                                        17

<210> SEQ ID NO 76
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
```
ataaactgtc aaaaggc                                                      17

<210> SEQ ID NO 77
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
ataaactgtc caaaaggc                                                     18

<210> SEQ ID NO 78
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
ataaactgac caaaaggc                                                     18

<210> SEQ ID NO 79
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
ataaactgtg caaaaggc                                                     18

<210> SEQ ID NO 80
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
ttaaagcgag ctccgaa                                                      17

<210> SEQ ID NO 81
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
ttaaagcgcg ctccgaa                                                      17

<210> SEQ ID NO 82
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
ttaaagcggg ctccgaa                                                      17

<210> SEQ ID NO 83
<211> LENGTH: 17
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 83
ttaaagcgtg ctccgaa                                                  17

<210> SEQ ID NO 84
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 84
ttaaagcgtt gctccgaa                                                 18

<210> SEQ ID NO 85
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 85
ttaaagcgta gctccgaa                                                 18

<210> SEQ ID NO 86
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 86
ttaaagcgct gctccgaa                                                 18

<210> SEQ ID NO 87
<211> LENGTH: 17
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 87
ccactctgat ggaagtg                                                  17

<210> SEQ ID NO 88
<211> LENGTH: 17
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 88
ccactctgct ggaagtg                                                  17

```
<210> SEQ ID NO 89
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
ccactctggt ggaagtg                                                  17

<210> SEQ ID NO 90
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
ccactctgtt ggaagtg                                                  17

<210> SEQ ID NO 91
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
ccactctgac tggaagtg                                                 18

<210> SEQ ID NO 92
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
ccactctgat tggaagtg                                                 18

<210> SEQ ID NO 93
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
ccactctgct tggaagtg                                                 18

<210> SEQ ID NO 94
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (5)..(22)
<223> OTHER INFORMATION: This region may encompass any of SEQ ID NOS 32,
      37, 42, or 73-93
```

<400> SEQUENCE: 94
ttagnnnnnn nnnnnnnnnn nntatc                                            26

<210> SEQ ID NO 95
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
actctgtgga ag                                                           12

<210> SEQ ID NO 96
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
actctgatgg aag                                                          13

<210> SEQ ID NO 97
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
actctgctgg aag                                                          13

<210> SEQ ID NO 98
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
actctggtgg aag                                                          13

<210> SEQ ID NO 99
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
actctgttgg aag                                                          13

<210> SEQ ID NO 100
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100

```
actctgactg gaag                                                       14

<210> SEQ ID NO 101
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
actctgattg gaag                                                       14

<210> SEQ ID NO 102
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
actctgcttg gaag                                                       14

<210> SEQ ID NO 103
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (26)..(39)
<223> OTHER INFORMATION: This region may encompass any of SEQ ID NOS
      95-102

<400> SEQUENCE: 103
gatctgttcg gagccgcttt aacccnnnnn nnnnnnnnnt gctcgcg                   47

<210> SEQ ID NO 104
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
aaagcggctc cg                                                         12

<210> SEQ ID NO 105
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
aaagcgagct ccg                                                        13

<210> SEQ ID NO 106
<211> LENGTH: 13
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 106
aaagcgcgct ccg                                                        13

<210> SEQ ID NO 107
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
aaagcgggct ccg                                                        13

<210> SEQ ID NO 108
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
aaagcgtgct ccg                                                        13

<210> SEQ ID NO 109
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
aaagcgttgc tccg                                                       14

<210> SEQ ID NO 110
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
aaagcgtagc tccg                                                       14

<210> SEQ ID NO 111
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
aaagcgctgc tccg                                                       14

<210> SEQ ID NO 112
<211> LENGTH: 47
<212> TYPE: DNA
<213> ORGANISM: Artificial Sequence
<220> FEATURE:
<223> OTHER INFORMATION: Description of Artificial Sequence: Synthetic
```

```
                      oligonucleotide
<220> FEATURE:
<221> NAME/KEY: misc_feature
<222> LOCATION: (9)..(22)
<223> OTHER INFORMATION: This region may encompass any of SEQ ID NOS
      104-111

<400> SEQUENCE: 112
gatctgttnn nnnnnnnnnn nnaacccact ctgtggaagt gctcgcg                    47

<210> SEQ ID NO 113
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
ataaactgaa caaaaggc                                                    18

<210> SEQ ID NO 114
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
ataaactgac caaaaggc                                                    18

<210> SEQ ID NO 115
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
ataaactgag caaaaggc                                                    18

<210> SEQ ID NO 116
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
ataaactgat caaaaggc                                                    18

<210> SEQ ID NO 117
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
ataaactgca caaaaggc                                                    18

<210> SEQ ID NO 118
<211> LENGTH: 18
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
ataaactgcc caaaaggc                                                   18

<210> SEQ ID NO 119
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
ataaactgcg caaaaggc                                                   18

<210> SEQ ID NO 120
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
ataaactgct caaaaggc                                                   18

<210> SEQ ID NO 121
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
ataaactgga caaaaggc                                                   18

<210> SEQ ID NO 122
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
ataaactggc caaaaggc                                                   18

<210> SEQ ID NO 123
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
ataaactggg caaaaggc                                                   18

<210> SEQ ID NO 124
<211> LENGTH: 18
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 124
ataaactggt caaaaggc                                                   18

<210> SEQ ID NO 125
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
ataaactgta caaaaggc                                                   18

<210> SEQ ID NO 126
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
ataaactgtc caaaaggc                                                   18

<210> SEQ ID NO 127
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
ataaactgtg caaaaggc                                                   18

<210> SEQ ID NO 128
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
ataaactgtt caaaaggc                                                   18

<210> SEQ ID NO 129
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Glu or Gln
<220> FEATURE:
<221> NAME/KEY: MOD_RES
<222> LOCATION: (4)..(4)
<223> OTHER INFORMATION: Lys or Arg

<400> SEQUENCE: 129
```

```
<210> SEQ ID NO 130
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Met Ala Glu Arg Pro Phe Gln Cys Arg Ile Cys Met Arg Asn Phe Ser
1               5                   10                  15

Arg Ser Asp Asn Leu Ser Val His Ile Arg Thr His Thr Gly Glu
            20                  25                  30

<210> SEQ ID NO 131
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Lys Pro Phe Ala Cys Asp Ile Cys Gly Arg Lys Phe Ala Gln Lys Ile
1               5                   10                  15

Asn Leu Gln Val His Thr Lys Ile His Thr Gly Glu
            20                  25

<210> SEQ ID NO 132
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Lys Pro Phe Gln Cys Arg Ile Cys Met Arg Asn Phe Ser Arg Ser Asp
1               5                   10                  15

Val Leu Ser Glu His Ile Arg Thr His Thr Gly Glu
            20                  25

<210> SEQ ID NO 133
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Lys Pro Phe Ala Cys Asp Ile Cys Gly Arg Lys Phe Ala Gln Arg Asn
1               5                   10                  15

His Arg Thr Thr His Thr Lys Ile His Leu Arg Gly Ser
            20                  25

<210> SEQ ID NO 134
<211> LENGTH: 31
<212> TYPE: PRT
<213> ORGANISM: Artificial Sequence
<220> FEATURE:
<223> OTHER INFORMATION: Description of Artificial Sequence: Synthetic
```

(Thr Gly Xaa Xaa Pro appears at top, position 1-5, as continuation from previous page)

-continued polypeptide

<400> SEQUENCE: 134

Met Ala Glu Arg Pro Phe Gln Cys Arg Ile Cys Met Arg Asn Phe Ser
1               5                   10                  15

Arg Ser Asp Asn Leu Ser Val His Ile Arg Thr His Thr Gly Glu
            20                  25                  30

<210> SEQ ID NO 135
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Lys Pro Phe Ala Cys Asp Ile Cys Gly Arg Lys Phe Ala Arg Asn Ala
1               5                   10                  15

His Arg Ile Asn His Thr Lys Ile His Thr Gly Ser Gln
            20                  25

<210> SEQ ID NO 136
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Lys Pro Phe Gln Cys Arg Ile Cys Met Arg Asn Phe Ser Arg Ser Asp
1               5                   10                  15

Asp Thr Ser Glu His Ile Arg Thr His Thr Gly Glu
            20                  25

<210> SEQ ID NO 137
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Lys Pro Phe Ala Cys Asp Ile Cys Gly Arg Lys Phe Ala Ala Arg Ser
1               5                   10                  15

Thr Arg Thr Asn His Thr Lys Ile His Leu Arg Gly Ser
            20                  25

<210> SEQ ID NO 138
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Met Ala Glu Arg Pro Phe Gln Cys Arg Ile Cys Met Arg Asn Phe Ser
1               5                   10                  15

Arg Ser Asp Thr Leu Ser Glu His Ile Arg Thr His Thr Gly Glu
            20                  25                  30

```
<210> SEQ ID NO 139
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Lys Pro Phe Ala Cys Asp Ile Cys Gly Arg Lys Phe Ala Ala Arg Ser
1               5                   10                  15

Thr Arg Thr Thr His Thr Lys Ile His Thr Gly Ser Gln
            20                  25

<210> SEQ ID NO 140
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Lys Pro Phe Gln Cys Arg Ile Cys Met Arg Asn Phe Ser Arg Ser Asp
1               5                   10                  15

Ser Leu Ser Lys His Ile Arg Thr His Thr Gly Glu
            20                  25

<210> SEQ ID NO 141
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Lys Pro Phe Ala Cys Asp Ile Cys Gly Arg Lys Phe Ala Gln Arg Ser
1               5                   10                  15

Asn Leu Lys Val His Thr Lys Ile His Leu Arg Gly Ser
            20                  25

<210> SEQ ID NO 142
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

His Thr Lys Ile His Thr Pro Asp Ala Pro Lys Pro Lys Pro Phe Gln
1               5                   10                  15

Cys Arg Ile Cys
            20

<210> SEQ ID NO 143
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

His Thr Lys Ile His Thr Pro Gly Leu His Arg Pro Lys Pro Phe Gln
```

Cys Arg Ile Cys
            20

<210> SEQ ID NO 144
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

His Thr Lys Ile His Met Glu Pro Arg Ala Lys Pro Pro Lys Pro Phe
1               5                   10                  15

Gln Cys Arg Ile Cys
            20

<210> SEQ ID NO 145
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

His Thr Lys Ile His Thr Pro Ser His Thr Pro Arg Pro Lys Pro Phe
1               5                   10                  15

Gln Cys Arg Ile Cys
            20

<210> SEQ ID NO 146
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

His Thr Lys Ile His Thr Gly Tyr Ser Ile Pro Arg Pro Lys Pro Phe
1               5                   10                  15

Gln Cys Arg Ile Cys
            20

<210> SEQ ID NO 147
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

His Thr Lys Ile His Thr Tyr Pro Arg Pro Ile Ala Ala Lys Pro Phe
1               5                   10                  15

Gln Cys Arg Ile Cys
            20

<210> SEQ ID NO 148
<211> LENGTH: 21
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 148

His Thr Lys Ile His Thr His Pro Arg Ala Pro Ile Pro Lys Pro Phe
1               5                   10                  15

Gln Cys Arg Ile Cys
            20

<210> SEQ ID NO 149
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

His Thr Lys Ile His Thr Pro Asn Arg Arg Pro Ala Pro Lys Pro Phe
1               5                   10                  15

Gln Cys Arg Ile Cys
            20

<210> SEQ ID NO 150
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

His Thr Lys Ile His Thr Ser Pro Arg Leu Pro Ala Pro Lys Pro Phe
1               5                   10                  15

Gln Cys Arg Ile Cys
            20

<210> SEQ ID NO 151
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

His Thr Lys Ile His Thr Cys Pro Arg Pro Pro Thr Arg Lys Pro Phe
1               5                   10                  15

Gln Cys Arg Ile Cys
            20

<210> SEQ ID NO 152
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

His Thr Lys Ile His Thr Ser Ser Pro Arg Ser Asn Ala Lys Pro Phe
1               5                   10                  15

Gln Cys Arg Ile Cys
            20
```

<210> SEQ ID NO 153
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

His Thr Lys Ile His Thr Val Ser Pro Ala Pro Cys Arg Ser Lys Pro
1               5                   10                  15

Phe Gln Cys Arg Ile Cys
            20

<210> SEQ ID NO 154
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

His Thr Lys Ile His Met Pro Asp Arg Pro Ile Ser Thr Cys Lys Pro
1               5                   10                  15

Phe Gln Cys Arg Ile Cys
            20

<210> SEQ ID NO 155
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

His Thr Lys Ile His Thr Pro Arg Pro Pro Ile Pro Lys Pro Phe Gln
1               5                   10                  15

Cys Arg Ile Cys
            20

<210> SEQ ID NO 156
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

His Thr Lys Ile His Thr Gln Pro Arg Gln Ile Pro Pro Lys Pro Phe
1               5                   10                  15

Gln Cys Arg Ile Cys
            20

<210> SEQ ID NO 157
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

His Thr Lys Ile His Thr Pro Asn Arg Cys Pro Pro Thr Lys Pro Phe
1               5                   10                  15

Gln Cys Arg Ile Cys
            20

<210> SEQ ID NO 158
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

His Thr Lys Ile His Thr Tyr Pro Arg Pro Leu Leu Ala Lys Pro Phe
1               5                   10                  15

Gln Cys Arg Ile Cys
            20

<210> SEQ ID NO 159
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

His Thr Lys Ile His Thr Pro Leu Cys Gln Arg Pro Met Lys Gln Lys
1               5                   10                  15

Pro Phe Gln Cys Arg Ile Cys
            20

<210> SEQ ID NO 160
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

His Thr Lys Ile His Thr Pro Leu Cys Gln Arg Pro Met Lys Gln Lys
1               5                   10                  15

Pro Phe Gln Cys Arg Ile Cys
            20

<210> SEQ ID NO 161
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

His Thr Lys Ile His Thr Gly Leu Pro Lys Pro Lys Pro Phe Gln Cys
1               5                   10                  15

Arg Ile Cys

<210> SEQ ID NO 162
<211> LENGTH: 19
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 162

His Thr Lys Ile His Thr Ser Arg Pro Arg Pro Lys Pro Phe Gln Cys
1               5                   10                  15

Arg Ile Cys

<210> SEQ ID NO 163
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

His Thr Lys Ile His Thr Leu Pro Leu Pro Arg Pro Lys Pro Phe Gln
1               5                   10                  15

Cys Arg Ile Cys
            20

<210> SEQ ID NO 164
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

His Thr Lys Ile His Thr Val Pro Arg Pro Thr Pro Pro Lys Pro Phe
1               5                   10                  15

Gln Cys Arg Ile Cys
            20

<210> SEQ ID NO 165
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

His Thr Lys Ile His Thr Leu Pro Pro Cys Phe Arg Pro Lys Pro Phe
1               5                   10                  15

Gln Cys Arg Ile Cys
            20

<210> SEQ ID NO 166
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

His Thr Lys Ile His Thr Leu Pro Pro Cys Phe Arg Pro Lys Pro Phe
1               5                   10                  15

Gln Cys Arg Ile Cys
            20

```
<210> SEQ ID NO 167
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

His Thr Lys Ile His Thr Asn Ala Cys Lys Pro Tyr Arg Thr Pro Lys
1               5                   10                  15

Pro Phe Gln Cys Arg Ile Cys
            20

<210> SEQ ID NO 168
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

His Thr Lys Ile His Thr Leu Ala Pro Arg Pro Tyr Arg Pro Pro Lys
1               5                   10                  15

Pro Phe Gln Cys Arg Ile Cys
            20

<210> SEQ ID NO 169
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

His Thr Lys Ile His Thr Gly Ser Pro His Val Arg Ala Asn Ser Gln
1               5                   10                  15

Pro Phe Gln Cys Arg Ile Cys
            20

<210> SEQ ID NO 170
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

His Thr Lys Ile His Thr Asp Ala Ala Pro Arg Arg Pro Arg Asp Thr
1               5                   10                  15

Lys Pro Phe Gln Cys Arg Ile Cys
            20

<210> SEQ ID NO 171
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

His Thr Lys Ile His Thr Glu Tyr Cys Thr Arg Pro Phe Arg Pro Pro
```

Lys Pro Phe Gln Cys Arg Ile Cys
            20

<210> SEQ ID NO 172
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

His Thr Lys Ile His Thr Pro Asn Pro His Arg Arg Tyr Asp Pro Ser
1               5                   10                  15

His Lys Pro Phe Gln Cys Arg Ile Cys
            20                  25

<210> SEQ ID NO 173
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

His Thr Lys Ile His Thr Asn Thr Pro Arg Pro Tyr Arg Leu Arg Pro
1               5                   10                  15

Pro Lys Pro Phe Gln Cys Arg Ile Cys
            20                  25

<210> SEQ ID NO 174
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

His Thr Lys Ile His Thr Pro Gly Gly Lys Ser Ser Arg Thr Asp Arg
1               5                   10                  15

Asn Lys Pro Phe Gln Cys Arg Ile Cys
            20                  25

<210> SEQ ID NO 175
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

His Thr Lys Ile His Thr Asn Thr Thr Arg Pro Tyr Arg Pro Pro Lys
1               5                   10                  15

Pro Phe Gln Cys Arg Ile Cys
            20

<210> SEQ ID NO 176
<211> LENGTH: 23
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 176

His Thr Lys Ile His Thr Asn Glu Arg Arg Pro Tyr Arg Pro Pro Lys
1               5                   10                  15

Pro Phe Gln Cys Arg Ile Cys
            20

<210> SEQ ID NO 177
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

His Thr Lys Ile His Thr Gly Ser Leu Arg Pro Tyr Arg Pro Pro Lys
1               5                   10                  15

Pro Phe Gln Cys Arg Ile Cys
            20

<210> SEQ ID NO 178
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

His Thr Lys Ile His Thr Gly Glu Ala Arg Pro Tyr Arg Pro Pro Lys
1               5                   10                  15

Pro Phe Gln Cys Arg Ile Cys
            20

<210> SEQ ID NO 179
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

His Thr Lys Ile His Thr Ser Ala Thr Thr Thr Tyr Arg Pro Pro Lys
1               5                   10                  15

Pro Phe Gln Cys Arg Ile Cys
            20

<210> SEQ ID NO 180
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

His Thr Lys Ile His Thr Ser Ala Pro Ser Thr Leu Ala Pro Pro Lys
1               5                   10                  15

Pro Phe Gln Cys Arg Ile Cys
            20
```

```
<210> SEQ ID NO 181
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

His Thr Lys Ile His Thr Pro Thr Thr Thr Leu Leu Arg Pro Pro Lys
1               5                   10                  15

Pro Phe Gln Cys Arg Ile Cys
            20

<210> SEQ ID NO 182
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

His Thr Lys Ile His Thr Asn Asp Ser Ala Pro Leu Arg Pro Pro Lys
1               5                   10                  15

Pro Phe Gln Cys Arg Ile Cys
            20

<210> SEQ ID NO 183
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

His Thr Lys Ile His Thr Glu Thr Thr Arg Pro Phe Arg Pro Pro Lys
1               5                   10                  15

Pro Phe Gln Cys Arg Ile Cys
            20

<210> SEQ ID NO 184
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

His Thr Lys Ile His Thr Ser Ile Asn Arg Pro Phe Arg Pro Pro Lys
1               5                   10                  15

Pro Phe Gln Cys Arg Ile Cys
            20

<210> SEQ ID NO 185
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185
```

His Thr Lys Ile His Thr Pro Met Pro Lys Gln Ser Tyr Arg Pro Pro
1               5                   10                  15

Lys Pro Phe Gln Cys Arg Ile Cys
            20

<210> SEQ ID NO 186
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

His Thr Lys Ile His Thr Glu Ala Ser Thr Ser Lys Tyr Arg Pro Pro
1               5                   10                  15

Lys Pro Phe Gln Cys Arg Ile Cys
            20

<210> SEQ ID NO 187
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

His Thr Lys Ile His Thr Val Asp Ser Thr Ala Thr Tyr Arg Pro Pro
1               5                   10                  15

Lys Pro Phe Gln Cys Arg Ile Cys
            20

<210> SEQ ID NO 188
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

His Thr Lys Ile His Thr Glu Pro Met Arg Gln Thr Tyr Arg Pro Pro
1               5                   10                  15

Lys Pro Phe Gln Cys Arg Ile Cys
            20

<210> SEQ ID NO 189
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

His Thr Lys Ile His Thr Asp Ser Pro Pro Ser Gln Tyr Arg Pro Pro
1               5                   10                  15

Lys Pro Phe Gln Cys Arg Ile Cys
            20

<210> SEQ ID NO 190
<211> LENGTH: 24
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 190

His Thr Lys Ile His Thr Pro Gln Ala His His Gly Leu Arg Pro Pro
1               5                   10                  15

Lys Pro Phe Gln Cys Arg Ile Cys
            20

<210> SEQ ID NO 191
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

His Thr Lys Ile His Thr Asn Ser Pro Ala Gln Ser Leu Arg Pro Pro
1               5                   10                  15

Lys Pro Leu Gln Cys Arg Ile Cys
            20

<210> SEQ ID NO 192
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

His Thr Lys Ile His Thr Gln Gly Thr Pro Thr Gln Leu Arg Pro Pro
1               5                   10                  15

Lys Pro Phe Gln Cys Arg Ile Cys
            20

<210> SEQ ID NO 193
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

His Thr Lys Ile His Thr Pro Asp Pro Pro Gly Ser Phe Arg Pro Pro
1               5                   10                  15

Lys Pro Phe Gln Cys Arg Ile Cys
            20

<210> SEQ ID NO 194
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

His Thr Lys Ile His Thr Ala Ser Cys Pro Arg Pro Phe Arg Pro Pro
1               5                   10                  15

Lys Pro Phe Gln Cys Arg Ile Cys
            20
```

```
<210> SEQ ID NO 195
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

His Thr Lys Ile His Thr Asp Thr Ser Ala Gln Arg Pro Leu Arg Pro
1               5                   10                  15

Pro Lys Pro Phe Gln Cys Arg Ile Cys
            20                  25

<210> SEQ ID NO 196
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

His Thr Lys Ile His Thr Gln Gly Asn Gln Ser Gly Tyr Leu Arg Pro
1               5                   10                  15

Pro Lys Pro Phe Gln Cys Arg Ile Cys
            20                  25

<210> SEQ ID NO 197
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

His Thr Lys Ile His Thr Pro Pro Gln Ala Ser Asp His Leu Arg Pro
1               5                   10                  15

Pro Lys Pro Phe Gln Cys Arg Ile Cys
            20                  25

<210> SEQ ID NO 198
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

His Thr Lys Ile His Thr Pro Ser Trp Pro Phe Ala Thr Leu Arg Pro
1               5                   10                  15

Pro Lys Pro Phe Gln Cys Arg Ile Cys
            20                  25

<210> SEQ ID NO 199
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199
```

```
His Thr Lys Ile His Thr Pro Ser Trp Pro Phe Ala Thr Leu Arg Pro
1               5                   10                  15

Pro Lys Pro Phe Gln Cys Arg Ile Cys
            20                  25

<210> SEQ ID NO 200
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

His Thr Lys Ile His Thr Asp Pro Ala Pro Pro Ala Pro Leu Arg Pro
1               5                   10                  15

Pro Lys Pro Phe Gln Cys Arg Ile Cys
            20                  25

<210> SEQ ID NO 201
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

His Thr Lys Ile His Thr Gln Thr Asp Arg Ala Pro Thr Leu Arg Pro
1               5                   10                  15

Pro Lys Pro Phe Gln Cys Arg Ile Cys
            20                  25

<210> SEQ ID NO 202
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

His Thr Lys Ile His Thr Thr Ser His Ser Arg Pro Thr Leu Arg Pro
1               5                   10                  15

Pro Lys Pro Phe Gln Cys Arg Ile Cys
            20                  25

<210> SEQ ID NO 203
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

His Thr Lys Ile His Thr Ala Met Lys Glu Ser Pro Ser Leu Pro Pro
1               5                   10                  15

Pro Lys Thr Phe Gln Cys Arg Ile Cys
            20                  25

<210> SEQ ID NO 204
<211> LENGTH: 25
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 204

His Thr Lys Ile His Thr Gly Asp Arg Thr Gln Leu Arg Phe Arg Pro
1               5                   10                  15

Pro Lys Pro Phe Gln Cys Arg Ile Cys
            20                  25

<210> SEQ ID NO 205
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

His Thr Lys Ile His Thr Pro Gly Thr Val Ser Ser Ala Phe Arg Pro
1               5                   10                  15

Pro Lys Pro Phe Gln Cys Arg Ile Cys
            20                  25

<210> SEQ ID NO 206
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

His Thr Lys Ile His Thr Asn Ile Pro Lys Ala Ser Pro Phe Arg Pro
1               5                   10                  15

Pro Lys Pro Phe Gln Cys Arg Ile Cys
            20                  25

<210> SEQ ID NO 207
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

His Thr Lys Ile His Thr Pro Thr Pro Tyr Gln Asn Ala Phe Arg Pro
1               5                   10                  15

Pro Lys Pro Phe Gln Cys Arg Ile Cys
            20                  25

<210> SEQ ID NO 208
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

His Thr Lys Ile His Thr Met Pro Asn Arg His Asn Glu Tyr Arg Pro
1               5                   10                  15

Pro Lys Pro Phe Gln Cys Arg Ile Cys

```
            20                  25

<210> SEQ ID NO 209
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

His Thr Lys Ile His Thr Ser Asn Lys Pro Pro Leu Arg Pro Pro
1               5                   10                  15

Lys Gln Thr Phe Gln Cys Arg Ile Cys
            20                  25

<210> SEQ ID NO 210
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

His Thr Lys Ile His Thr Ser Asn Lys Pro Pro Leu Arg Pro Pro
1               5                   10                  15

Lys Gln Thr Phe Gln Cys Arg Ile Cys
            20                  25

<210> SEQ ID NO 211
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (27)..(38)
<223> OTHER INFORMATION: Any amino acid and this region may encompass
      2-12 residues

<400> SEQUENCE: 211

Lys Pro Phe Ala Cys Asp Ile Cys Gly Arg Lys Phe Ala Arg Asn Ala
1               5                   10                  15

His Arg Ile Asn His Thr Lys Ile His Thr Xaa Xaa Xaa Xaa Xaa Xaa
            20                  25                  30

Xaa Xaa Xaa Xaa Xaa Xaa
        35

<210> SEQ ID NO 212
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (27)..(38)
<223> OTHER INFORMATION: Any amino acid and this region may encompass
      2-12 residues

<400> SEQUENCE: 212

Lys Pro Phe Ala Cys Asp Ile Cys Gly Arg Lys Phe Ala Ala Arg Ser
1               5                   10                  15
```

-continued

```
Thr Arg Thr Thr His Thr Lys Ile His Thr Xaa Xaa Xaa Xaa Xaa Xaa
            20                  25                  30

Xaa Xaa Xaa Xaa Xaa Xaa
        35

<210> SEQ ID NO 213
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (27)..(33)
<223> OTHER INFORMATION: Any amino acid and this region may encompass
      5-7 residues
<220> FEATURE:
<221> NAME/KEY: MOD_RES
<222> LOCATION: (34)..(34)
<223> OTHER INFORMATION: Phe, Leu, or Tyr

<400> SEQUENCE: 213

Lys Pro Phe Ala Cys Asp Ile Cys Gly Arg Lys Phe Ala Gln Lys Ile
1               5                   10                  15

Asn Leu Gln Val His Thr Lys Ile His Thr Xaa Xaa Xaa Xaa Xaa Xaa
            20                  25                  30

Xaa Xaa Arg Pro Pro
        35
```